US008497236B2

(12) United States Patent
Benedict et al.

(10) Patent No.: US 8,497,236 B2
(45) Date of Patent: *Jul. 30, 2013

(54) IMPLANTABLE PUTTY MATERIAL

(75) Inventors: James J. Benedict, Arvada, CO (US); Christopher J. Damien, Denver, CO (US)

(73) Assignee: Zimmer Orthobiologics, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/180,035

(22) Filed: Jul. 25, 2008

(65) Prior Publication Data

US 2008/0293617 A1 Nov. 27, 2008

Related U.S. Application Data

(60) Continuation of application No. 10/739,492, filed on Dec. 17, 2003, now abandoned, which is a division of application No. 09/023,617, filed on Feb. 13, 1998, now Pat. No. 6,679,918.

(51) Int. Cl.
*A61K 38/00* (2006.01)

(52) U.S. Cl.
USPC ............................. 514/1.1; 514/773; 424/423

(58) Field of Classification Search
None
See application file for complete search history.

(56) References Cited

U.S. PATENT DOCUMENTS

| | | |
|---|---|---|
| 2,471,598 A | 5/1949 | Wilt et al. |
| 3,368,911 A | 2/1968 | Kuntz et al. |
| 3,393,080 A | 7/1968 | Erdi et al. ................ 106/161 |
| 3,443,261 A | 5/1969 | Battista et al. ................ 3/1 |
| 3,471,598 A | 10/1969 | Battista |
| 3,767,437 A | 10/1973 | Cruz, Jr. |
| 3,949,073 A | 4/1976 | Daniels et al. ............ 424/177 |
| 4,066,083 A | 1/1978 | Ries |
| 4,273,705 A | 6/1981 | Kato ....................... 260/123.7 |
| 4,294,753 A | 10/1981 | Urist ........................ 260/112 R |
| 4,356,572 A | 11/1982 | Guillemin et al. ............ 3/1.9 |
| 4,389,487 A | 6/1983 | Ries |
| 4,394,370 A | 7/1983 | Jefferies ..................... 424/15 |
| 4,412,947 A | 11/1983 | Cioca |
| 4,430,760 A | 2/1984 | Smestad |
| 4,440,680 A * | 4/1984 | Cioca ....................... 530/356 |
| 4,440,750 A * | 4/1984 | Glowacki et al. ......... 424/572 |
| 4,472,840 A | 9/1984 | Jefferies |
| 4,485,097 A | 11/1984 | Bell |
| 4,516,276 A | 5/1985 | Mittelmeier et al. ......... 3/1.91 |
| 4,557,764 A * | 12/1985 | Chu .......................... 106/160.1 |
| 4,563,350 A | 1/1986 | Nathan et al. ................ 424/95 |
| 4,563,489 A | 1/1986 | Urist |
| 4,596,574 A | 6/1986 | Urist ........................ 623/16 |
| 4,600,533 A | 7/1986 | Chu |
| 4,637,931 A | 1/1987 | Schmitz ..................... 424/78 |
| 4,656,130 A | 4/1987 | Shoshan ..................... 435/30 |
| 4,689,399 A | 8/1987 | Chu |
| 4,703,108 A | 10/1987 | Silver et al. ................ 530/356 |
| 4,725,671 A | 2/1988 | Chu et al. |
| 4,743,229 A | 5/1988 | Chu ............................ 604/82 |
| 4,774,227 A | 9/1988 | Piez et al. ..................... 514/21 |
| 4,776,890 A | 10/1988 | Chu |
| 4,789,663 A | 12/1988 | Wallace et al. ............ 514/21 |
| 4,795,467 A | 1/1989 | Piez et al. ................... 623/16 |
| 4,839,215 A | 6/1989 | Starling et al. |
| 4,863,732 A | 9/1989 | Nathan et al. .............. 424/95 |
| 4,865,602 A | 9/1989 | Smestad et al. ............ 623/16 |
| 4,888,366 A * | 12/1989 | Chu et al. .................. 523/115 |
| 4,948,540 A | 8/1990 | Nigam |
| 4,950,483 A | 8/1990 | Ksander et al. ............ 424/422 |
| 4,970,298 A | 11/1990 | Silver et al. ................ 530/356 |
| 4,975,526 A | 12/1990 | Kuberasampath et al. ... 530/350 |
| 4,975,527 A | 12/1990 | Koezuka et al. ............ 530/356 |
| 4,992,226 A | 2/1991 | Piez et al. ................... 264/109 |
| 5,001,169 A | 3/1991 | Nathan et al. .............. 523/113 |
| 5,024,841 A | 6/1991 | Chu et al. ................... 424/422 |
| 5,035,715 A | 7/1991 | Smestad et al. ............ 623/16 |
| 5,071,436 A | 12/1991 | Huc et al. .................. 623/16 |
| 5,073,373 A | 12/1991 | O'Leary et al. ............ 424/422 |
| 5,084,051 A | 1/1992 | Tormala et al. |
| 5,090,815 A | 2/1992 | Bohle |
| 5,108,436 A | 4/1992 | Chu et al. ................... 623/66 |
| 5,110,604 A | 5/1992 | Chu et al. |
| 5,123,925 A | 6/1992 | Smestad et al. ............ 623/16 |
| 5,133,755 A | 7/1992 | Brekke et al. |
| 5,158,934 A | 10/1992 | Ammann et al. |
| 5,171,579 A | 12/1992 | Ron et al. |
| 5,231,169 A | 7/1993 | Constantz et al. ............ 530/356 |
| 5,236,456 A | 8/1993 | O'Leary et al. ............ 623/16 |
| 5,246,457 A | 9/1993 | Piez et al. ................... 623/16 |
| 5,270,300 A | 12/1993 | Hunziker .................. 514/12 |
| 5,273,964 A | 12/1993 | Lemons .................... 514/2 |
| 5,290,494 A | 3/1994 | Coombes et al. |
| 5,290,763 A * | 3/1994 | Poser et al. ............... 514/21 |
| 5,314,476 A | 5/1994 | Prewett et al. ............ 623/16 |
| 5,332,802 A | 7/1994 | Kelman et al. |
| 5,338,772 A | 8/1994 | Bauer et al. ............... 523/115 |

(Continued)

FOREIGN PATENT DOCUMENTS

| AU | 2007334213 B2 | 8/2012 |
|---|---|---|
| CA | 2133253 A1 | 3/1996 |

(Continued)

OTHER PUBLICATIONS

Ho et al., Journal of controlled release, 1997, vol. 44, p. 103-11.*

(Continued)

*Primary Examiner* — Kade Ariani
(74) *Attorney, Agent, or Firm* — Schwegman, Lundberg & Woessner P.A.

(57) ABSTRACT

The present invention provides compositions for an implantable putty material for delivery of active compounds to a patient. More specifically, the present invention provides a material having a pH of between about 3 and 6 and possessing putty-like physical properties, wherein the composition of the material includes collagen and water. The present invention also provides a method for using the implantable putty material.

18 Claims, 5 Drawing Sheets

U.S. PATENT DOCUMENTS

| | | | |
|---|---|---|---|
| 5,354,557 A | 10/1994 | Oppermann et al. | 424/423 |
| 5,366,498 A | 11/1994 | Brannan et al. | 623/11 |
| 5,371,191 A | 12/1994 | Poser et al. | |
| 5,376,375 A | 12/1994 | Rhee et al. | 424/423 |
| 5,393,739 A | 2/1995 | Bentz et al. | 514/12 |
| 5,397,572 A | 3/1995 | Coombes et al. | |
| 5,405,390 A | 4/1995 | O'Leary et al. | 623/16 |
| 5,475,052 A | 12/1995 | Rhee et al. | |
| 5,492,697 A | 2/1996 | Boyan et al. | |
| 5,507,813 A | 4/1996 | Dowd et al. | |
| 5,522,894 A | 6/1996 | Draenert | 623/23.61 |
| 5,532,217 A | 7/1996 | Silver et al. | 514/21 |
| 5,563,124 A | 10/1996 | Damien et al. | |
| 5,618,549 A | 4/1997 | Patat et al. | 424/422 |
| 5,674,290 A | 10/1997 | Li | 424/423 |
| 5,676,146 A | 10/1997 | Scarborough | |
| 5,676,699 A | 10/1997 | Gogolewski et al. | 623/16.11 |
| 5,677,284 A | 10/1997 | Li | |
| 5,679,723 A | 10/1997 | Cooper et al. | |
| 5,683,459 A | 11/1997 | Brekke | |
| 5,707,962 A * | 1/1998 | Chen et al. | 514/12 |
| 5,733,337 A | 3/1998 | Carr, Jr. et al. | |
| 5,739,286 A | 4/1998 | Silver et al. | 530/356 |
| 5,776,193 A | 7/1998 | Kwan et al. | 424/423 |
| 5,824,084 A | 10/1998 | Muschler | |
| 5,916,870 A | 6/1999 | Lee et al. | |
| 5,919,408 A | 7/1999 | Muller et al. | |
| 5,948,428 A | 9/1999 | Lee et al. | |
| 5,948,429 A | 9/1999 | Bell et al. | |
| 6,048,964 A | 4/2000 | Lee et al. | |
| 6,123,957 A | 9/2000 | Jernberg | |
| 6,132,468 A | 10/2000 | Mansmann | |
| 6,180,606 B1 | 1/2001 | Chen et al. | 514/12 |
| 6,183,737 B1 | 2/2001 | Zaleske et al. | 424/93.7 |
| 6,187,047 B1 | 2/2001 | Kwan et al. | 623/16.11 |
| 6,201,039 B1 | 3/2001 | Brown et al. | |
| 6,203,573 B1 | 3/2001 | Walter et al. | 623/16.11 |
| 6,203,574 B1 | 3/2001 | Kawamura | 623/16.11 |
| 6,241,771 B1 | 6/2001 | Gresser et al. | |
| 6,300,315 B1 | 10/2001 | Liu | 514/21 |
| 6,311,690 B1 | 11/2001 | Jefferies | 128/898 |
| 6,335,007 B1 | 1/2002 | Shimizu et al. | 424/78.08 |
| 6,383,519 B1 | 5/2002 | Sapieszko et al. | |
| 6,384,196 B1 | 5/2002 | Weis et al. | |
| 6,384,197 B1 | 5/2002 | Weis et al. | |
| 6,406,498 B1 | 6/2002 | Tormala et al. | 623/23.75 |
| 6,454,787 B1 | 9/2002 | Maddalo et al. | |
| 6,461,630 B1 | 10/2002 | Tucker et al. | |
| 6,471,993 B1 | 10/2002 | Shastri et al. | |
| 6,504,079 B2 | 1/2003 | Tucker et al. | |
| 6,506,217 B1 | 1/2003 | Arnett | |
| 6,511,510 B1 | 1/2003 | Bruijn et al. | 623/23.56 |
| 6,514,514 B1 | 2/2003 | Atkinson et al. | 424/423 |
| 6,521,246 B2 | 2/2003 | Sapieszko et al. | |
| 6,547,866 B1 | 4/2003 | Edwards et al. | |
| 6,548,002 B2 | 4/2003 | Gresser et al. | |
| 6,551,355 B1 | 4/2003 | Lewandrowski et al. | |
| 6,582,471 B1 | 6/2003 | Bittmann et al. | 623/23.63 |
| 6,589,590 B2 | 7/2003 | Czernuszka et al. | |
| 6,602,294 B1 | 8/2003 | Sittinger et al. | |
| 6,645,250 B2 | 11/2003 | Schulter | |
| 6,679,918 B1 | 1/2004 | Benedict et al. | 623/23.61 |
| 6,696,073 B2 | 2/2004 | Boyce et al. | |
| 6,712,822 B2 | 3/2004 | Re et al. | |
| 6,736,799 B1 | 5/2004 | Erbe et al. | |
| 6,840,961 B2 | 1/2005 | Tofighi et al. | |
| 6,884,621 B2 | 4/2005 | Liao et al. | |
| 6,899,107 B2 | 5/2005 | Lewandrowski et al. | |
| 6,911,046 B2 | 6/2005 | Schulter | |
| 6,911,212 B2 | 6/2005 | Gertzman et al. | 424/426 |
| 6,921,412 B1 | 7/2005 | Black et al. | |
| 6,933,326 B1 | 8/2005 | Griffey et al. | |
| 6,953,594 B2 | 10/2005 | Lee et al. | |
| 6,974,862 B2 | 12/2005 | Ringeisen et al. | |
| 6,991,803 B2 | 1/2006 | Sapieszko et al. | |
| 7,026,292 B1 | 4/2006 | Lee et al. | |
| 7,052,517 B2 | 5/2006 | Murphy et al. | |
| 7,077,866 B2 | 7/2006 | Gresser et al. | |
| 7,122,057 B2 | 10/2006 | Beam et al. | |
| 7,132,110 B2 | 11/2006 | Kay et al. | |
| 7,156,880 B2 | 1/2007 | Evans et al. | |
| 7,163,691 B2 | 1/2007 | Knaack et al. | |
| 7,166,133 B2 | 1/2007 | Evans et al. | |
| 7,175,858 B2 | 2/2007 | Constantz et al. | |
| 7,189,263 B2 | 3/2007 | Erbe et al. | |
| 7,235,107 B2 | 6/2007 | Evans et al. | |
| 7,241,316 B2 | 7/2007 | Evans et al. | |
| 7,250,550 B2 | 7/2007 | Overby et al. | |
| 7,252,685 B2 | 8/2007 | Bindseil et al. | |
| 7,252,841 B2 | 8/2007 | Constantz | |
| 7,303,814 B2 | 12/2007 | Lamberti et al. | |
| 7,318,840 B2 | 1/2008 | McKay | |
| 7,318,841 B2 | 1/2008 | Tofighi et al. | |
| 7,358,284 B2 | 4/2008 | Griffey et al. | |
| 7,473,678 B2 | 1/2009 | Lynch | |
| 7,485,617 B1 | 2/2009 | Pohl et al. | |
| 7,494,950 B2 | 2/2009 | Armitage et al. | |
| 7,498,040 B2 | 3/2009 | Masinaei et al. | |
| 7,498,041 B2 | 3/2009 | Masinaei et al. | |
| 7,517,539 B1 | 4/2009 | Lee et al. | |
| 7,531,004 B2 | 5/2009 | Bagga et al. | |
| 7,534,264 B2 | 5/2009 | Fischer | |
| 7,534,451 B2 | 5/2009 | Erbe et al. | |
| 7,621,963 B2 | 11/2009 | Simon et al. | |
| 7,628,851 B2 | 12/2009 | Armitage et al. | |
| 7,670,378 B2 | 3/2010 | Bloemer et al. | |
| 7,670,384 B2 | 3/2010 | Kimar et al. | |
| 7,686,239 B2 | 3/2010 | Tofighi et al. | |
| 7,722,895 B1 | 5/2010 | McKay et al. | |
| 7,771,741 B2 | 8/2010 | Drapeau et al. | |
| 7,776,100 B2 | 8/2010 | Brekke et al. | |
| 7,780,994 B2 | 8/2010 | Lynn et al. | |
| 7,785,617 B2 | 8/2010 | Shakesheff et al. | |
| 7,799,767 B2 | 9/2010 | Lamberti et al. | |
| 7,811,608 B2 | 10/2010 | Kay et al. | |
| 7,824,702 B2 | 11/2010 | Wironen et al. | |
| 7,833,278 B2 | 11/2010 | Evans et al. | |
| 7,857,860 B2 | 12/2010 | Saini et al. | |
| 7,887,598 B2 | 2/2011 | Evans et al. | |
| 7,887,831 B2 | 2/2011 | Yayon | |
| 7,892,291 B2 | 2/2011 | Evans et al. | |
| 7,897,722 B2 | 3/2011 | Chung et al. | |
| 7,910,690 B2 | 3/2011 | Ringeisen et al. | |
| 7,951,200 B2 | 5/2011 | Heinz | |
| 7,959,941 B2 | 6/2011 | Knaack et al. | |
| 7,963,997 B2 | 6/2011 | Brekke et al. | |
| 8,029,575 B2 | 10/2011 | Borden | |
| 2002/0018796 A1 | 2/2002 | Wironen | |
| 2002/0076429 A1 | 6/2002 | Wironen et al. | 424/426 |
| 2002/0082220 A1 | 6/2002 | Hoemann et al. | 514/21 |
| 2002/0114795 A1 | 8/2002 | Thorne et al. | |
| 2002/0128722 A1 | 9/2002 | Jefferies | 623/23.51 |
| 2003/0009235 A1 | 1/2003 | Manrique et al. | |
| 2003/0036797 A1 | 2/2003 | Malaviya et al. | |
| 2003/0143207 A1 | 7/2003 | Livesey et al. | |
| 2003/0236573 A1 | 12/2003 | Evans et al. | 623/23.58 |
| 2004/0002558 A1 | 1/2004 | McKay | 523/115 |
| 2004/0062816 A1 | 4/2004 | Atkinson et al. | 424/549 |
| 2004/0081704 A1 | 4/2004 | Benedict et al. | |
| 2004/0181232 A1 | 9/2004 | Re et al. | |
| 2004/0197311 A1 | 10/2004 | Brekke et al. | |
| 2005/0079201 A1 | 4/2005 | Rathenow et al. | |
| 2005/0249773 A1 | 11/2005 | Maspero et al. | |
| 2005/0251266 A1 | 11/2005 | Maspero et al. | |
| 2005/0261767 A1 | 11/2005 | Anderson et al. | |
| 2005/0283255 A1 | 12/2005 | Geremakis et al. | |
| 2005/0288795 A1 | 12/2005 | Bagga et al. | |
| 2006/0030627 A1 | 2/2006 | Yamamoto et al. | |
| 2006/0030948 A1 | 2/2006 | Manrique et al. | |
| 2006/0039951 A1 | 2/2006 | Sapieszko et al. | |
| 2006/0147547 A1 | 7/2006 | Yayon | |
| 2006/0184131 A1 | 8/2006 | Murphy et al. | |
| 2006/0216321 A1 | 9/2006 | Lyu et al. | |
| 2006/0233851 A1 | 10/2006 | Simon et al. | |
| 2006/0246150 A1 | 11/2006 | Thorne | 424/603 |
| 2006/0251729 A1 | 11/2006 | Kay et al. | |
| 2007/0003593 A1 | 1/2007 | Wironen et al. | |

| | | | | | | |
|---|---|---|---|---|---|---|
| 2007/0071791 A1 | 3/2007 | Fischer | EP | 0 171 176 | | 2/1986 |
| 2007/0088437 A1 | 4/2007 | Betz et al. | EP | 0 233 770 A2 | | 8/1987 |
| 2007/0093912 A1 | 4/2007 | Borden | EP | 289562 A1 | | 11/1988 |
| 2007/0128249 A1 | 6/2007 | McKay | EP | 309241 A2 | | 3/1989 |
| 2007/0129807 A1 | 6/2007 | Lynch et al. | EP | 321277 A2 | | 6/1989 |
| 2007/0134285 A1 | 6/2007 | Lynn et al. | EP | 0349048 A2 | | 1/1990 |
| 2007/0154563 A1 | 7/2007 | Behnam et al. | EP | 0361896 A2 | | 4/1990 |
| 2007/0178158 A1 | 8/2007 | Knaack et al. | EP | 0 243 178 B1 | | 6/1991 |
| 2007/0191963 A1 | 8/2007 | Winterbottom et al. | EP | 0197693 B1 | | 10/1991 |
| 2007/0202148 A1 | 8/2007 | Ringeisen et al. | EP | 271668 B1 | | 12/1991 |
| 2007/0231788 A1 | 10/2007 | Behnam et al. | EP | 321277 B1 | | 3/1992 |
| 2007/0233272 A1 | 10/2007 | Boyce et al. | EP | 522569 A1 | | 1/1993 |
| 2007/0248575 A1 | 10/2007 | Connor et al. | EP | 289562 B1 | | 2/1993 |
| 2007/0276489 A1 | 11/2007 | Bindseil et al. | EP | 0 270 254 B1 | | 3/1993 |
| 2008/0015692 A1 | 1/2008 | Heinz | EP | 0567391 A1 | | 10/1993 |
| 2008/0015709 A1 | 1/2008 | Evans et al. | EP | 0309241 B1 | | 12/1993 |
| 2008/0033548 A1 | 2/2008 | Xuenong et al. | EP | 309241 B1 | | 12/1993 |
| 2008/0033572 A1 | 2/2008 | D'antonio et al. | EP | 573491 A1 | | 12/1993 |
| 2008/0063671 A1 | 3/2008 | Morris et al. | EP | 0 446 262 B1 | | 3/1994 |
| 2008/0065210 A1 | 3/2008 | McKay | EP | 0605933 B1 | | 7/1994 |
| 2008/0069852 A1 | 3/2008 | Shimp et al. | EP | 608313 A1 | | 8/1994 |
| 2008/0095815 A1 | 4/2008 | Mao | EP | 0 621 044 A2 | | 10/1994 |
| 2008/0114458 A1 | 5/2008 | McKay | EP | 0668478 B1 | | 10/1994 |
| 2008/0124397 A1 | 5/2008 | Wironen et al. | EP | 0439689 B1 | | 12/1994 |
| 2008/0145392 A1 | 6/2008 | Knaack et al. | EP | 627899 A1 | | 12/1994 |
| 2008/0145404 A1 | 6/2008 | Hill et al. | EP | 0 674 908 A1 | | 10/1995 |
| 2008/0147065 A1 | 6/2008 | McKay et al. | EP | 732947 A1 | | 9/1996 |
| 2008/0147197 A1 | 6/2008 | McKay | EP | 855884 B1 | | 4/1997 |
| 2008/0152687 A1 | 6/2008 | Thorne | EP | 828453 A1 | | 3/1998 |
| 2008/0188945 A1 | 8/2008 | Boyce et al. | EP | 837701 A1 | | 4/1998 |
| 2008/0199508 A1 | 8/2008 | Lamberti et al. | EP | 855884 A1 | | 8/1998 |
| 2008/0233203 A1 | 9/2008 | Woodell-May et al. | EP | 0588727 B1 | | 11/1998 |
| 2008/0241211 A1 | 10/2008 | Han | EP | 0605799 B1 | | 4/1999 |
| 2008/0249637 A1 | 10/2008 | Asgari et al. | EP | 0932373 A1 | | 8/1999 |
| 2008/0262613 A1 | 10/2008 | Gogolewski | EP | 1795214 A2 | | 8/1999 |
| 2008/0317817 A1 | 12/2008 | Fischer | EP | 608313 B1 | | 2/2000 |
| 2009/0012625 A1 | 1/2009 | Ying et al. | EP | 0623031 B1 | | 2/2000 |
| 2009/0017093 A1 | 1/2009 | Springer et al. | EP | 1019027 A1 | | 7/2000 |
| 2009/0123547 A1 | 5/2009 | Hill et al. | EP | 1120439 A1 | | 8/2001 |
| 2009/0124552 A1 | 5/2009 | Hill et al. | EP | 627899 B1 | | 11/2001 |
| 2009/0142385 A1 | 6/2009 | Gross et al. | EP | 1150659 | | 11/2001 |
| 2009/0148495 A1 | 6/2009 | Hammer et al. | EP | 1150725 A1 | | 11/2001 |
| 2009/0155366 A1 | 6/2009 | Pohl et al. | EP | 1150726 A1 | | 11/2001 |
| 2009/0157182 A1 | 6/2009 | Koblish et al. | EP | 1178769 A1 | | 2/2002 |
| 2009/0246244 A1 | 10/2009 | McKay et al. | EP | 1180986 A2 | | 2/2002 |
| 2009/0254104 A1 | 10/2009 | Murray | EP | 732947 B1 | | 3/2002 |
| 2009/0292359 A1 | 11/2009 | Borden | EP | 573491 B1 | | 4/2002 |
| 2009/0292360 A1 | 11/2009 | Borden | EP | 1233714 A1 | | 8/2002 |
| 2009/0292367 A1 | 11/2009 | Borden | EP | 1234587 A1 | | 8/2002 |
| 2009/0324675 A1 | 12/2009 | Gunatillake et al. | EP | 0719529 B1 | | 9/2002 |
| 2010/0004733 A1 | 1/2010 | Atanasoska et al. | EP | 837701 B1 | | 2/2003 |
| 2010/0015230 A1 | 1/2010 | Ron | EP | 0987031 B1 | | 4/2003 |
| 2010/0021520 A1 | 1/2010 | Baskin et al. | EP | 1434608 A2 | | 4/2003 |
| 2010/0036503 A1 | 2/2010 | Chen et al. | EP | 1482872 A1 | | 9/2003 |
| 2010/0048763 A1 | 2/2010 | Armitage et al. | EP | 1150726 B1 | | 11/2003 |
| 2010/0049322 A1 | 2/2010 | McKay | EP | 1019027 A4 | | 5/2004 |
| 2010/0049330 A1 | 2/2010 | Horvath | EP | 1416977 A2 | | 5/2004 |
| 2010/0082072 A1 | 4/2010 | Sybert et al. | EP | 1419791 A1 | | 5/2004 |
| 2010/0098673 A1 | 4/2010 | D'Antonnio et al. | EP | 0855884 B1 | | 6/2004 |
| 2010/0131074 A1 | 5/2010 | Shikinami | EP | 1120439 B1 | | 6/2004 |
| 2010/0168869 A1 | 7/2010 | Long et al. | EP | 1425024 A2 | | 6/2004 |
| 2010/0196489 A1 | 8/2010 | Thorne | EP | 1 437 148 A1 | | 7/2004 |
| 2010/0209408 A1 | 8/2010 | Livesey | EP | 1462126 A1 | | 9/2004 |
| 2010/0209470 A1 | 8/2010 | Mohan et al. | EP | 1476202 A1 | | 11/2004 |
| 2010/0226961 A1 | 9/2010 | Lamberti et al. | EP | 1476204 A1 | | 11/2004 |
| 2010/0255115 A1 | 10/2010 | Mohan et al. | EP | 1677846 | | 5/2005 |
| 2010/0266658 A1 | 10/2010 | McKay et al. | EP | 1150725 B1 | | 6/2005 |
| 2010/0266660 A1 | 10/2010 | McKay et al. | EP | 1545466 A1 | | 6/2005 |
| 2010/0268227 A1 | 10/2010 | Tong et al. | EP | 1701672 | | 7/2005 |
| 2011/0045044 A1 | 2/2011 | Masinaei et al. | EP | 1701729 | | 7/2005 |
| 2011/0133368 A1 | 6/2011 | Ringeisen et al. | EP | 1561480 A2 | | 8/2005 |
| 2011/0140137 A1 | 6/2011 | Lai | EP | 1708651 A1 | | 8/2005 |
| 2011/0144767 A1 | 6/2011 | Evans et al. | EP | 1727489 A1 | | 8/2005 |
| 2011/0183936 A1 | 7/2011 | Bailleul | EP | 1727489 A2 | | 8/2005 |
| 2012/0121660 A1 | 5/2012 | Akella et al. | EP | 828453 B1 | | 11/2005 |
| | | | EP | 1234587 B1 | | 11/2005 |
| FOREIGN PATENT DOCUMENTS | | | EP | 1608414 A2 | | 12/2005 |
| CA | 2446840 A1 | 4/2002 | EP | 1623681 A1 | | 2/2006 |
| CA | 2280966 C | 4/2012 | EP | 1638486 A2 | | 3/2006 |

| | | | |
|---|---|---|---|
| EP | 1648347 | | 4/2006 |
| EP | 1178769 | B1 | 7/2006 |
| EP | 1712244 | A1 | 10/2006 |
| EP | 1753474 | A2 | 2/2007 |
| EP | 1771490 | A1 | 4/2007 |
| EP | 1940313 | | 5/2007 |
| EP | 1976459 | | 7/2007 |
| EP | 1976460 | | 7/2007 |
| EP | 1839622 | A2 | 10/2007 |
| EP | 1844798 | A1 | 10/2007 |
| EP | 2007196 | | 11/2007 |
| EP | 1925325 | A1 | 5/2008 |
| EP | 1608414 | B1 | 7/2008 |
| EP | 2125055 | | 9/2008 |
| EP | 1476204 | B1 | 10/2008 |
| EP | 2139500 | | 10/2008 |
| EP | 1476202 | B1 | 1/2009 |
| EP | 2049591 | A1 | 4/2009 |
| EP | 2070491 | A2 | 6/2009 |
| EP | 2104518 | A2 | 9/2009 |
| EP | 1464345 | B1 | 12/2009 |
| EP | 2129318 | A2 | 12/2009 |
| EP | 1419791 | B1 | 2/2010 |
| EP | 1416977 | B1 | 7/2010 |
| EP | 2260790 | A2 | 12/2010 |
| EP | 1233714 | B1 | 2/2012 |
| GB | 1 224 925 | | 3/1971 |
| GB | 2164042 | A | 3/1986 |
| GB | 02377642 | A | 1/2003 |
| JP | 61226055 | A | 10/1986 |
| JP | 11506727 | A | 6/1999 |
| JP | 11313882 | A | 11/1999 |
| JP | 11313883 | A | 11/1999 |
| JP | 2000262608 | A | 9/2000 |
| JP | 2002501786 | A | 1/2002 |
| JP | 2004520106 | A | 7/2004 |
| JP | 5105216 | A | 10/2012 |
| WO | WO8904646 | A | 6/1989 |
| WO | WO92/09697 | | 6/1992 |
| WO | WO-9316739 | A1 | 9/1993 |
| WO | WO93/20857 | | 10/1993 |
| WO | WO94/02412 | | 2/1994 |
| WO | WO-9415653 | A1 | 7/1994 |
| WO | WO95/25550 | | 9/1995 |
| WO | WO98/40113 | | 7/1998 |
| WO | WO98/35653 | | 8/1998 |
| WO | WO-9835653 | A1 | 8/1998 |
| WO | WO-9858602 | A1 | 12/1998 |
| WO | WO-9919003 | A1 | 4/1999 |
| WO | WO-0045870 | A1 | 8/2000 |
| WO | WO-0045871 | A1 | 8/2000 |
| WO | WO-0047114 | A1 | 8/2000 |
| WO | WO01/30409 | | 5/2001 |
| WO | WO02/051449 | | 7/2002 |
| WO | WO02051449 | A2 | 7/2002 |
| WO | WO-02051449 | A3 | 7/2002 |
| WO | WO02/070029 | | 9/2002 |
| WO | WO2005004755 | A1 | 1/2005 |
| WO | WO-2008019024 | A2 | 2/2008 |
| WO | WO2008076604 | A1 | 6/2008 |
| WO | WO-2009052967 | A1 | 4/2009 |
| WO | WO-2010117766 | A1 | 10/2010 |
| WO | WO-2010119476 | A2 | 10/2010 |
| WO | WO-2010134102 | A1 | 11/2010 |
| WO | WO-2012068135 | A1 | 5/2012 |

OTHER PUBLICATIONS

Ronziere et al., Osteoarthritis and Cartilage, 1997, vol. 5, p. 205-214.*
Oxlund et al. J Anat., 1980, vol. 131, No. 4, p. 611-620.*
Rosenblatt et al. Biomaterials, 1994, vol. 15, No. 12, p. 985-995.*
Itoh et al. Jpn. J. Appl. Phys., 1996, vol. 35, Part 1, No. 12A, p. 6172-6179.*
Ho et al., Journal of Controlled Release, 1997, vol. 44, p. 103-112.*
Bentz et al., *The Journal of Biological Chemistry* 264(32):20805-20810 (Dec. 5, 1989).
Bentz et al., *Matrix* 11:269-275 (1991).
Block et al., *Laboratory Medicine* 13(5):290-298 (May 1982).
Burwell, *Clinical Orthopaedics and Related Research*, "The Function of Bone Marrow in the Incorporation of a Bone Graft," pp. 125-141 (Nov. 1985).
Cheng et al., *The Journal of Bone & Joint Surgery* 85-A(8):1544-1552 (Aug. 2003).
*Chondrogenesis and Osteogenesis: Growth Factors* (913-921), p. 162a, Abstract Nos. 917-921 (date unknown).
"Collagraft® Bone Graft Matrix (Nonosteoinductive Bone Void Filler)," distributed by Zimmer, Inc., Warsaw, Indiana (Sep. 10, 1992).
"Collagraft® Bone Graft Matrix (Indications)," distributed by Zimmer, Inc., Warsaw, Indiana (Sep. 10, 1992).
"Collagraft® Bone Graft Matrix Strip," distributed by Zimmer, Inc., Warsaw, Indiana, pp. 1-6 (Feb. 1994).
"Collagraft® Bone Graft Matrix (Contraindications)," distributed by Zimmer, Inc., Warsaw, Indiana (Sep. 10, 1992).
"Collagraft™ Bone Graft Substitute (Physician Package Insert)," distributed by Zimmer, Inc., Warsaw, Indiana (Mar. 1989).
Collagraft™ Bone Graft Substitute, distributed by Zimmer, Inc., Warsaw, Indiana (Mar. 1989).
Cornell et al., *Journal of Orthopaedic Trauma* 5(1):1-8 (1991).
Cornell, *Techniques in Orthopaedics* 7(2):55-63 (1992).
Damien et al., *Journal of Applied Biomaterials* 2:187-208 (1991).
DeLustro et al., *Clinical Orthopaedics and Related Research* 260:263-279 (Nov. 1990).
Endres et al., *Tissue Engineering* 9(4):689-702 (2003).
Guillemin et al., *J. Biomed. Mat. Res.* 21:557-567 (1987).
Hott et al., "Ceramics in Substitutive and Reconstructive Surgery," P. Vincenzini, ed., pp. 345-352 (1991).
Kocialkowski et al., *Injury* 21:142-144 (1990).
Kocialkowski et al., *Bone Grafts, Derivatives & Substitutes*, "Collagraft Combined with Autogeneic Bone Marrow: Experimental and Clinical Results," Chapter 14, pp. 271-290 (1994).
Lane et al., *J. Orthop. Trauma* 2(1):57-58 (1988) (abstract).
McIntyre et al., *Ceramic Bulletin* 70(9):1499-1503 (1991).
Medtronic Sofamor Danek, http://www.medtronicsofamordanek.com/patient-spinal-infuse.html (Jan. 23, 2004).
Muschler et al., *Journal of Orthopaedic Research* 11:514-524 (1993).
Nathan et al., *Journal of Orthopaedic Research* 6:324-334 (1988).
Peng et al., *J. Cell Biochem.* 90(6):1149-1165 (Dec. 15, 2003), http://www.ncbi.nlm.nih.gov/entrez/query.fcgi?cmd=Retrieve&db=PubMed&list_uids=14 (Jan. 23, 2004).
Ronzière et al., *Osteoarthritis and Cartilage* 5:205-214 (1997).
Sampath et al., *Proc. Natl. Acad. Sci. USA* 84:7109-7113 (Oct. 1987).
Stryker Biotech OP-1 Osteogenic Protein-1 Implant Bone Morphogenetic Protein-7 BMP, http://www.opl.com/home.cfm?countryID=5 (Jan. 23, 2004).
Takagi et al., *Clinical Orthopaedics and Related Research* 171:224-231 (Nov.-Dec. 1982).
Zardiackas et al., *Journal of Applied Biomaterials* 5:277-283 (1994).
Zerwekh et al., *Journal of Orthopaedic Research* 10:562-572 (1992).
"Evaluation of a Bovine-Derived Osteoinductive Bone Protein in a Nonhuman Primate Model of Lumbar Spinal Fusion," *American Academy of Orthopaedic Surgeons 1996 Annual Meeting—Scientific Program*, http://www.aaos.org/wordhtml/anmeet96/sciprog/073.htm (Jan. 4, 1996).
"Characterization of Osteoinductive Potential," *Orthovita Products*, http://www.orthovita.com/products/vitoss/osteoinductive.html (Jan. 23, 2004).
"2714 Osteoinductive Implants: The mis-en-scène for drug-bearing biomimetic coatings," *Osteoinductive Implants*, http://iadr.confex.com/iadr/2004Hawaii/techprogram/abstract_40044.htm (Jan. 23, 2004).
"Osteoinductive," http://www.scientific.net/Osteoinductive.htm (Jan. 23, 2004).
Kubler, et al., "Bone Morphogenetic Protein-Mediated Interaction of Periosteum and Diaphysis Citric Acid and Other Factors Influencing the Generation of Parosteal Bone," Clinical Orthopaedics & Related Research, No. 258, Sep. 1990, pp. 279-294, USA.
Noah, et al., "Impact of Sterilization on the Porus Design and Cell Behavior in Collagen Sponges prepared for Tissue Engineering," Biomaterials 23 (2002) pp. 2855-2861, Elsevier, Germany.

Stone, et al., "Porcine and Bovine Cartilage Transplants in Cynomolgus Monkey," Transplantation, vol. 63, No. 5, Mar. 15, 1997, pp. 640-645, Williams & Wilkins, USA.

Truumees, et al., "Alternatives to Autologous Bone Harvest in Spine Surgery," The University of Pennsylvania Orthopaedic Journal 12, 1999, pp. 77-88, USA.

"Canadian Application Serial No. 2,280,966, Office Action mailed Apr. 27, 2011", 2 pgs.

Oxlund, H., et al., "The roles of hyaluronic acid, collagen and elastin in the mechanical properties of connective tissues", J Anat., 131(Pt 4), (Dec. 1980), 611-20.

"U.S. Appl. No. 12/849,414 , Response filed Mar. 23, 2012 to Non Final Office Action mailed Sep. 23, 2011", 8 pgs.

"Australian Application Serial No. 2007334213, Response filed Apr. 19, 2012 to First Examiners Report mailed Dec. 9, 2012", 9 pgs.

"Japanese Application Serial No. 1998535914, Office Action Mailed Jan. 24, 2012", W/ English Translation, 24 Pgs.

Cheung, D. T, et al., "The effect of gamma-irradiation on collagen molecules, isolated alpha-chains, and crosslinked native fibers.", J Biomed Mater Res., 24(5), (May 1990), 581-9.

Chu, C. C, et al., "The effect of gamma irradiation on the enzymatic degradation of polyglycolic acid absorbable sutures", J Biomed Mater Res., 17(6), (Nov. 1983), 1029-40.

Hallfeldt, K. K, et al., "Sterilization of partially demineralized bone matrix: the effects of different sterilization techniques on osteogenetic properties", J Surg Res., 59(5), (Nov. 1995), 614-20.

Hamada, K., et al., "Hydrothermal modification of titanium surface in calcium solutions", Biomaterials, 23, (2002), 2265-2272.

Ho, Hsiu-O, et al., "Characterization of collagen isolation and application of collagen gel as a drug carrier", Journal of Controlled Release, 44, (1997), 103-112.

Ijiri, S., et al., "Effect of sterilization on bone morphogenetic protein", J Orthop Res., 12(5), (Sep. 1994), 628-36.

Katz, R. W, et al., "Radiation-sterilized insoluble collagenous bone matrix is a functional carrier of osteogenin for bone induction", Calcif Tissue Int., 47(3), (Sep. 1990), 183-5.

Kim, H. M, et al., "Effect of heat treatment on apatite-forming ability of Ti metal induced by alkali treatment", J Mater Sci Mater Med., 8(6), (Jun. 1997), 341-7.

Lee, K. Y, et al., "Preparation of Caclium Phosphate Paste Composites with Demineralized Bone Matrix", Key Engineering Materials, (vols. 330-332), (2007), 803-806.

Legeros, Racquel Zapanta, "Calcium Phosphate-Based Osteoinductive Materials", Chem. Rev., 108, (2008), 4742-4753.

Liu, B., et al., "The effect of gamma irradiation on injectable human amnion collagen", J Biomed Mater Res., 23(8), (Aug. 1989), 833-44.

Munting, E., et al., "Effect of sterilization on osteoinduction. Comparison of five methods in demineralized rat bone", Acta Orthop Scand., 59(1), (Feb. 1988), 34-8.

Puolakkainen, "The effect of sterilization on transforming growth factor beta isolated from demineralized human bone", Transfusion, 33(8), (Aug. 1993), 679-85.

Raptopoulou-Gigi, M., et al., "Antimicrobial proteins in sterilised human milk", Br Med J., 1(6052), (Jan. 1, 1977), 12-4.

Reid, B. D, et al., "Gamma processing technology: an alternative technology for terminal sterilization of parenterals", PDA J Pharm Sci Technol., 49(2), (Mar.-Apr. 1995), 83-9.

Schwarz, N., et al., "Irradiation-sterilization of rat bone matrix gelatin", Acta Orthop Scand., 59(2), (Apr. 1988), 165-7.

Soboleva, N. N, et al., "Radiation resistivity of frozen insulin solutions and suspensions", Int J Appl Radiat Isot., 32(10), (Oct. 1981), 753-6.

Su, D., et al., "Sterilization of collagen matrix containing protein growth factors using gamma and electron beam irradiation", Pharmaceutical Research, 12(9), Abstract BIOTEC 2035, (1995), S-87.

Tezcaner, A., et al., "Fundamentals of tissue engineering: Tissues and applications", Technology and Health Care, 10, (2002), 203-216.

Tofighi, A., "Calcium Phosphate Cement (CPC): A Critical Development Path", Key Engineering Materials, (vols. 361-363), (2008), 303-306.

Wientroub, S., et al., "Influence of irradiation on the osteoinductive potential of demineralized bone matrix", Calcif Tissue Int., 42(4), (Apr. 1988), 255-60.

U.S. Appl. No. 12/849,414, Response filed Nov. 1, 2012 to Final Office Action mailed Aug. 1, 2012, 8 pgs.

U.S. Appl. No. 12/849,414, Final Office Action mailed Aug. 1, 2012, 20 pgs.

U.S. Appl. No. 13/297,005, Non Final Office Action mailed Oct. 10, 2012, 13 pgs.

U.S. Appl. No. 13/297,005, Response filed Jan. 10, 2013 to Non Final Office Action mailed Oct. 10, 2012, 10 pgs.

"Canadian Application Serial No. 2,673,337, Office Action mailed Aug. 9, 2012", 3 pgs.

"Canadian Application Serial No. 2,673,337, Response filed Feb. 7, 2013 to Office Action mailed Aug. 9, 2012", 7 pgs.

"Japanese Application Serial No. 1998535914, Response filed Jul. 24, 2012 to Office Action mailed Jan. 24, 2012", (w/ English Translation of Claims), 16 pgs.

"Japanese Application Serial No. 2009-543018, Office Action mailed Dec. 4, 2012", (w/ English Translation), 5 pgs.

"Tri-Calcium Phosphates as a Biomaterial", [Online]. Retrieved from the Internet: <URL: http://www.scribd.com/doc/56970573/Tri-Calcium-Phosphates-as-a-Biomaterial>, (Upload Date: Jun. 2, 2011), 5 pgs.

Chakkalakal, D A, et al., "Mineralization and pH relationships in healing skeletal defects grafted with demineralized bone matrix", Journal of Biomedical Materials Research vol. 28,, (1994), 1439-1443.

Clarke, K. I., et al., "Investigation into the Formation and Mechanical Properties of a Bioactive Material Based on Collagen and Calcium Phosphate", Journal of Materials Science in Medicine, 4, (1993), 107-110.

Donlon, William, "Immune Neutrality of Calf Skin Collagen Gel Used to Stimulate Revitalization in Pulpless Open Apex Teeth of Rhesus Monkeys", J Dent Res, (Jun. 1977), 670-673.

Kohles, S S, et al., "A Morphometric Evaluation of Allograft Matrix Combinations in the Treatment of Osseous Defects in a Baboon Model", Calcif. Tissue Int. 67, (2000), 156-162.

Legeros, R Z, et al., "In Vitro Formation of Dicalcium Phosphate Dihydrate, $CaHPO_4.2h_2o$ (DCPD)", Scanning Electron Micropscopy, (1983), 407-418.

Legeros, R Z, et al., "The Nature of the Calcified Material Induced by Collagen-Calcium Phosphate Gel in Tooth", Dental Research vol. 57, Special Issue A, Abstract only. Abstract No. 527, (Jan. 1978), 206.

Legeros, Racquel Z, "Biodegradation and Bioresorption of Calcium Phosphate Ceramics", Clinical Materials 14, (1993), 65-88.

Legeros, Raquel Zapanta, "Apatites in Biological Systems", Prog. Crystal Growth Charact. vol. 4, (1981), 1-45.

Lenart, G, et al., "Some Basic Problems in the Examination of the Calcium Hydrogen Phosphates of Bone", Clinical Orthopaedics and Related Research, (1972), 263-272.

Nancollas, G H, et al., "Seeded Growth of Calcium Phosphates: Effect of Different Calcium Phosphate Seed Material", J. Dent. Res. vol. 55, No. 4, (1976), 617-624.

Nevins, Alan, et al., "Hard Tissue Induction Into Pulpless Open-Apex Teeth Using Collagen-Calcium Phosphate Gel", Journal of Endodontics vol. 3, Iss. 11, (1977), 431-433.

Nevins, Alan, et al., "Revitalization of pulpless open apex teeth in rhesus monkeys, using collagen-calcium phosphate gel", J Endod. 2(6), (1976), 159-65.

Roufosse, A. H, "Indentification of Burshite in Newly Deposited Bone Mineral from Embryonic Chicks", Journal of Ultrastructure Research 68, (1979), 235-255.

Tenhuisen, Kevor S, et al., "Formation and properties of a synthetic bone composite: Hydroxyapatite-collagen", Journal of Biomedical Materials Research vol. 29, (1995), 803-810.

Walsh, W R, et al., "Demineralized bone Matrix as a template for mineral-organic composites", Biomaterials 16, (1995), 1363-1371.

"U.S. Appl. No. 12/748,999, Response filed Mar. 1, 2012 to Final Office Action mailed Nov. 1, 2011", 6 pgs.

"Canadian Application Serial No. 2,280,966, Office Action Oct. 3, 2007", 2 pgs.

"Canadian Application Serial No. 2,280,966, Office Action mailed Jul. 30, 2006", 2 pgs.

"Canadian Application Serial No. 2,280,966, Office Action mailed Nov. 9, 2009", 3 pgs.

"Canadian Application Serial No. 2,280,966, Response filed Jan. 29, 2007 to Office Action mailed Jul. 31, 2006", 7 pgs.

"Canadian Application Serial No. 2,280,966, Response filed Mar. 28, 2008 to Office Action mailed Oct. 3, 2007", 12 pgs.

"Canadian Application Serial No. 2,280,966, Response filed May 5, 2010 to Office Action mailed Nov. 9, 2009", 5 pgs.

"European Application Serial No. 01991379.7, Office Action mailed Jun. 17, 2005", 5 pgs.

"European Application Serial No. 07013717.9, European Search Report mailed Sep. 4, 2007", 8 pgs.

"European Application Serial No. 07013717.9, European Search Report mailed Sep. 10, 2007", 5 pgs.

"European Application Serial No. 07013717.9, Office Action mailed Apr. 1, 2008", 2 pgs.

"European Application Serial No. 07864863.1, Office Action mailed Nov. 6, 2009", 5 pgs.

"European Application Serial No. 07864863.1, Response filed Mar. 16, 2010 to Office Action mailed Nov. 6, 2009", 10 pgs.

"European Application Serial No. 98908535.2, Office Action mailed Feb. 1, 2006", 4 pgs.

"European Application Serial No. 98908535.2, Office Action mailed Feb. 2, 2005", 4 pgs.

"European Application Serial No. 98908535.2, Office Action mailed Nov. 6, 2006", 3 pgs.

"European Application Serial No. 98908535.2, Response filed May 29, 2006 to Office Action mailed Feb. 1, 2006", 9 pgs.

"European Application Serial No. 98908535.2, Response filed Aug. 2, 2005 to Office Action mailed Feb. 2, 2005", 8 pgs.

"European Application Serial No. 98908535.2, Search Report mailed Mar. 25, 2004", 3 pgs.

"International Application Serial No. PCT/US2001/049314, International Preliminary Examination Report mailed Oct. 24, 2002", 2 pgs.

"International Application Serial No. PCT/US2007/085853, International Preliminary Report on Patentability mailed Jun. 23, 2009", 8 pgs.

"International Application Serial No. PCT/US2007/085853, International Search Report mailed Jul. 3, 2008", 4 pgs.

"Japanese Application Serial No. 1998535914, Office Action mailed Sep. 30, 2008", 3 pgs.

"Japanese Application Serial No. 1998535914, Response filed Aug. 10, 2009", w/Translation, 40 pgs.

"Japanese Application Serial No. 2002-552590, Office Action mailed Mar. 31, 2009", 4 pgs.

"Japanese Application Serial No. 2002-552590, Office Action mailed Aug. 19, 2008", 6 pgs.

Landesman, Richard, et al., "In Vivo Analysis of the Half-Life of the Osteoinductive Potential of Demineralized Bone Matrix Using Diffusion Chambers", Calcif Tissue Int. vol. 45, (1989), 348-353.

Pappalardo, S, et al., "How to biomaterials affect the biological activities and responses of cells? An in-vitro study", Minerva Stomatol vol. 59, (2010), 445-464.

Urist, Marshall R, et al., "Preservation and Biodegration of the Morphogenetic Property of Bone Matrix", J. theor. Biol. vol. 38, (1973), 155-167.

"Fundamentals of Bone Physiology", Therics, (Jul. 2006), 5 pgs.

"The Organization of Skeletal Tissues", The Architecture and Cellular Elements of Bone, (Oct. 2000), 4 pgs.

\* cited by examiner

IMPLANTABLE PUTTY MATERIAL

CROSS-REFERENCE TO RELATED APPLICATIONS

This application is a continuation of U.S. patent application Ser. No. 10/739,492, filed Dec. 17, 2003 now abandoned, which is a divisional of U.S. patent application Ser. No. 09/023,617, filed Feb. 13, 1998, now U.S. Pat. No. 6,679,918, which claims priority to Provisional Application No. 60/037,071, which are incorporated by reference in their entirety.

FIELD OF THE INVENTION

The present invention relates to an implantable putty material for delivery of active compounds to a patient.

BACKGROUND OF THE INVENTION

A wide variety of implantable materials have been used in the delivery of active compounds to a patient. For example, such materials can be used in the repair of bone defects. Typically, these materials are implanted at a desired site to promote bone growth. Ideally, such a material should have the ability to adhere and conform to the implanted site and facilitate bone growth.

U.S. Pat. Nos. 5,314,476 and 5,073,373 disclose a deformable, shape-sustaining osteogenic composition comprising demineralized bone particles and a polyhydroxy compound such as glycerol, or an oligosaccharide.

U.S. Pat. Nos. 5,405,390 and 5,236,456 disclose a surface-adherent osteogenic composition derived from demineralized and thermally modified bone tissue. The composition is administered in the form of a powder, a viscous liquid, or by direct injection.

U.S. Pat. No. 5,246,457 discloses a bone-repair composition comprising a calcium phosphate salt and reconstituted fibrillar atelopeptide collagen. It does not include any biologically active ingredients. The physical and handling properties are improved by a number of curing processes, including heat, maturation of the wet mixture and/specific cross-linking of collagen.

U.S. Pat. No. 4,440,750 discloses an osteogenic composition comprising demineralized bone powder and reconstituted native atelopeptide collagen fibers in a continuous aqueous phase having a substantially physiologic pH and ionic strength.

U.S. Pat. No. 4,975,526 discloses a matrix material comprising protein-extracted demineralized bone powder and a swelling agent to increase the intraparticle porosity of the matrix.

U.S. Pat. No. 4,394,370 discloses a bone graft material for treating osseous defects. The material comprises collagen and demineralized bone particles and is sponge-like.

Currently known implantable materials, including those discussed above, are lacking in acceptable texture properties, such as cohesiveness, elasticity and the ability to be molded to a selected shape. Moreover, other paste-like materials such as those disclosed in U.S. Pat. Nos. 5,314,476 and 5,073,373 require an organic solvent such as glycerol, as discussed above.

Therefore, there is a need for an osteoinductive material which have an improved handling properties and which does not require an organic solvent.

SUMMARY OF THE INVENTION

One embodiment of the present invention is a putty material which includes collagen and water, wherein the putty material has a pH of between about 3.0 to about 6.0. Materials of the invention have excellent physical properties and handling characteristics. The collagen of the putty material can be selected from the group consisting of fibrillar coltagen, atelopeptide collagen, telopeptide collagen and tropocollagen. The putty material can be formed by the addition of an acid selected from the group consisting of ascorbic acid, acetic acid, acetyl salicylic acid, benzoic acid, citric acid, glutamic acid, glycolic acid, lactic acid, malic acid, salicylic acid, and hydrochloric acid. The putty material can also include an active ingredient, such as an active ingredient selected from the group consisting of osteoinductive materials, growth factors, cartilage inducing factors, angiogenic factors, hormones, antibiotics, and antiviral compounds.

Another embodiment of the present invention is an osteogenic composition which includes collagen, an osteoinductive material, and an acid, wherein the osteogenic composition includes between about 0.05 mmol of acid per 100 mg of the collagen to about 2.3 mmol of acid per 100 mg of the collagen.

Another embodiment of the present invention is an osteogenic composition which includes bovine tendon Type I collagen, ascorbic acid, water, bone growth protein and a demineralized bone material.

Another embodiment of the present invention is a composition produced from a process including the steps of admixing collagen, an acid, and water to form a gel; and adding a demineralized bone material to said gel to produce an osteogenic putty, wherein the osteogenic putty has a pH of about 6.0 or less.

Another embodiment of the present invention is a process for making a dry osteoinductive composition comprising the steps of admixing collagen, an acid, an osteoinductive material and water to form a gel; and lyophilizing said gel.

Another embodiment of the present invention is a method for administering an active compound to a patient comprising the steps of preparing a delivery vehicle by admixing collagen and an acid to form a composition having a pH of between about 3.0 and about 6.0, incorporating an active compound into the delivery vehicle and implanting the delivery vehicle in a desired portion of the patient's body.

DETAILED DESCRIPTION OF THE INVENTION

Figure 1:
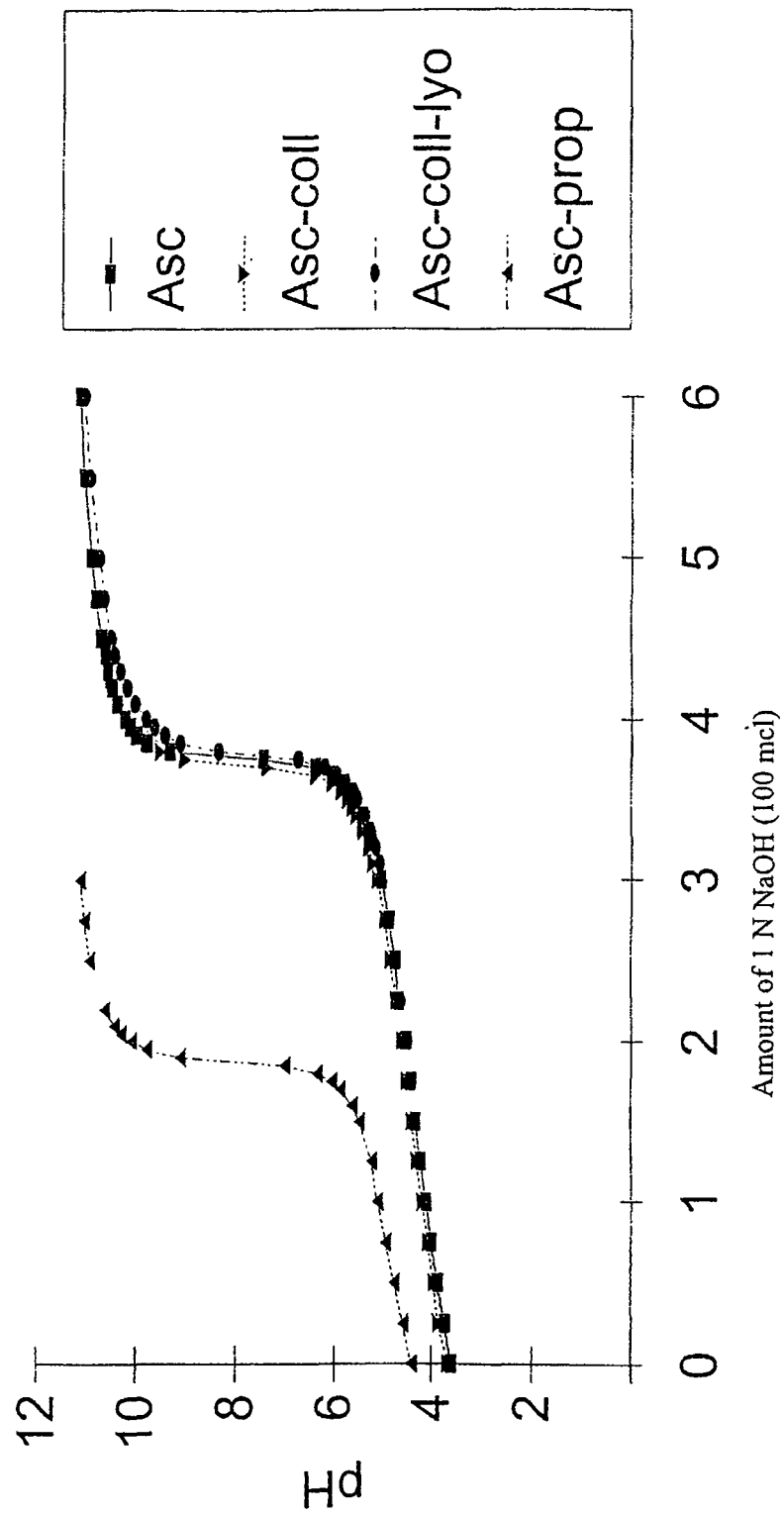
FIG. 1 illustrates volatility of ascorbic acid from an implantable material during lyophilization process.
Figure 2:
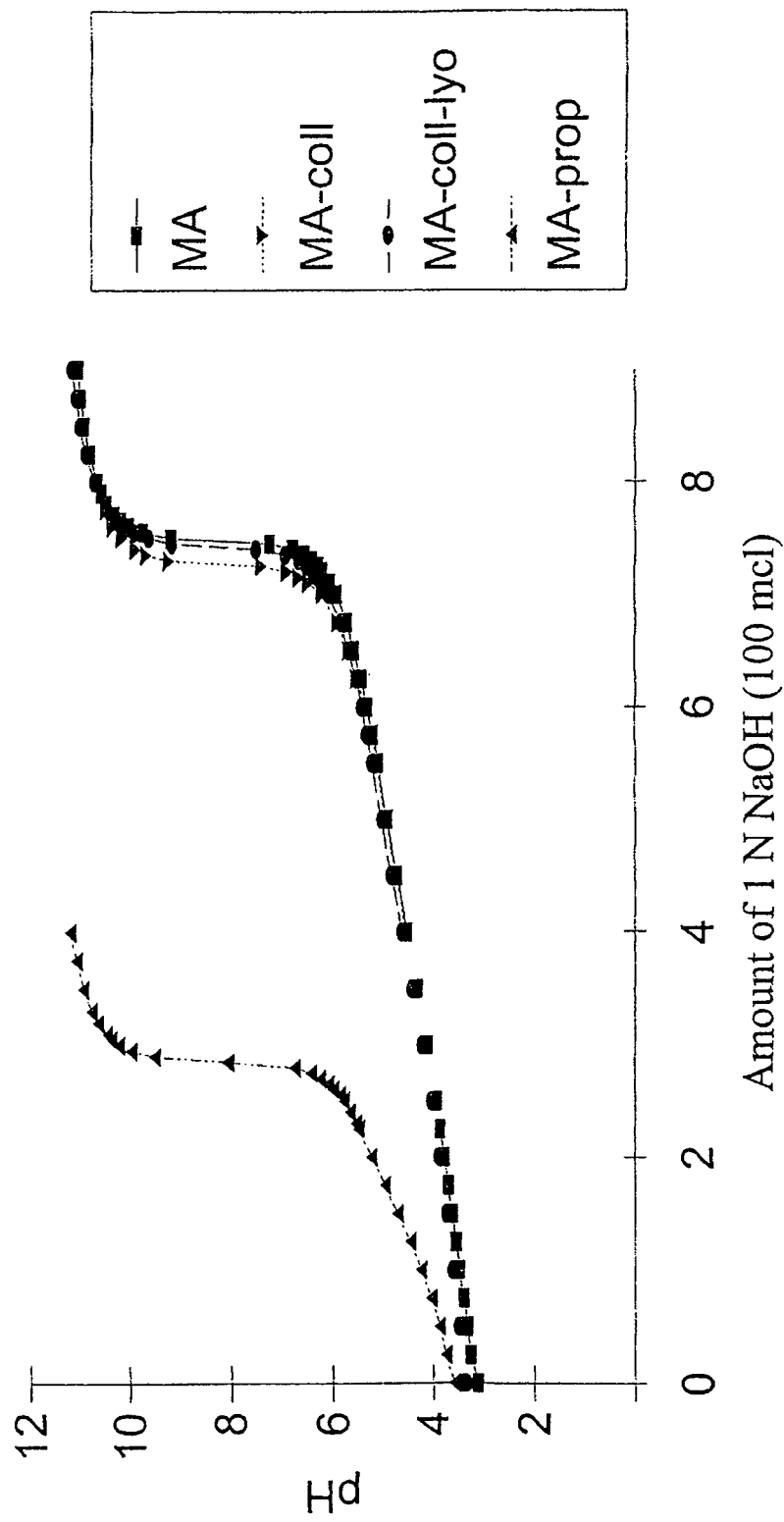
FIG. 2 illustrates volatility of malic acid from an implantable material during lyophilization process.
Figure 3:
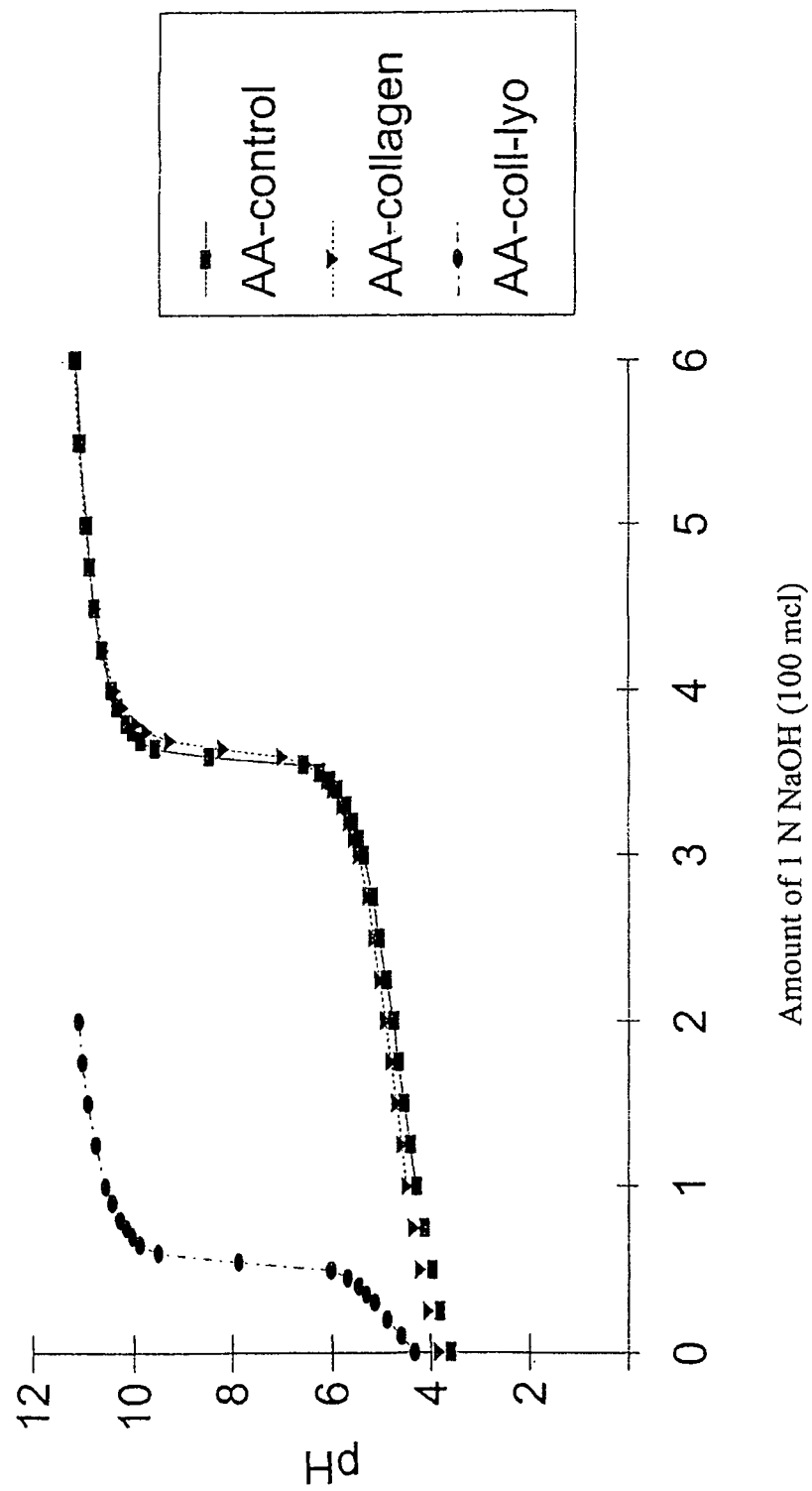
FIG. 3 illustrates volatility of acetic acid from an implantable material during lyophilization process.
Figure 4:
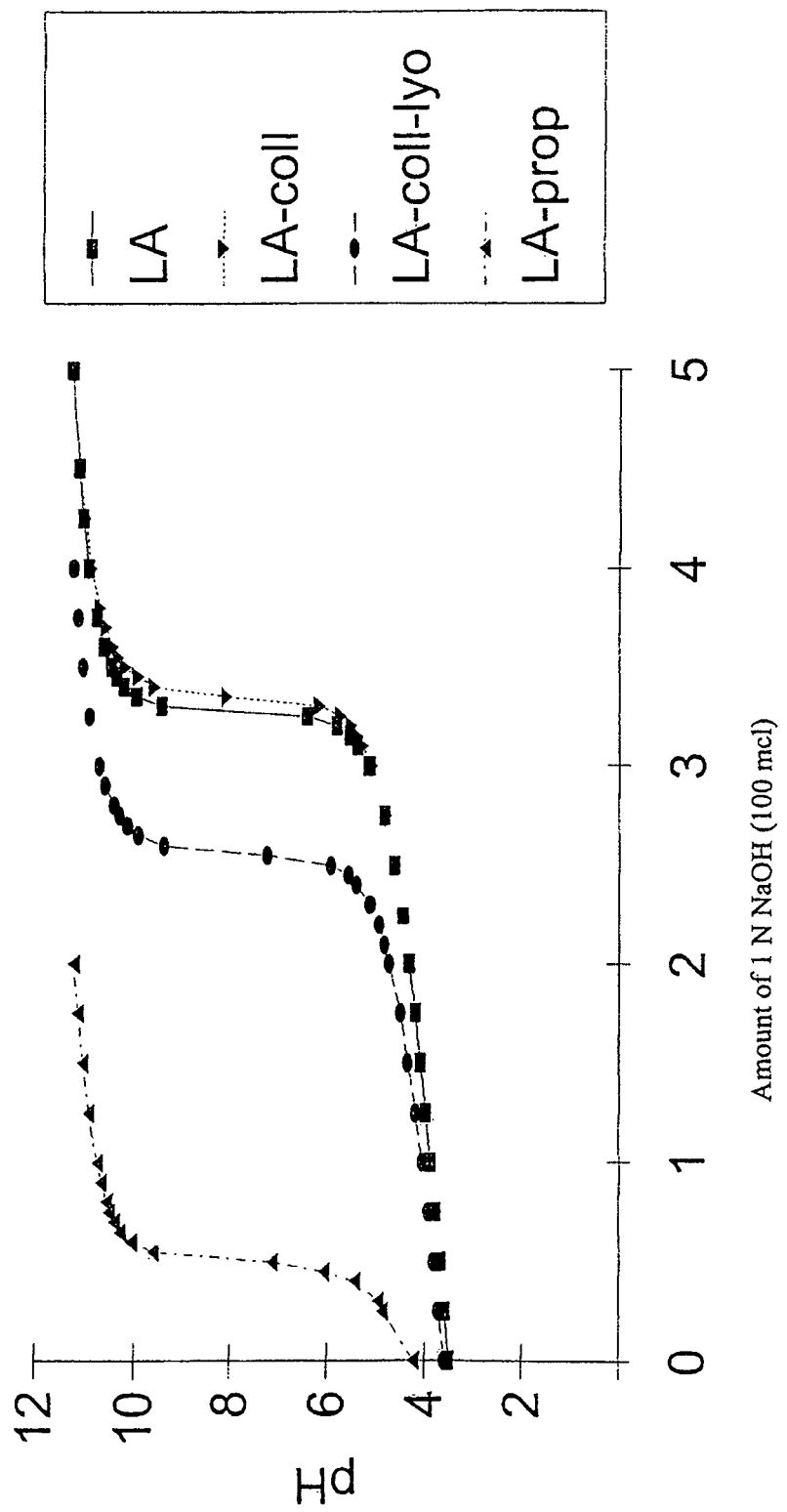
FIG. 4 illustrates volatility of lactic acid from an implantable material during lyophilization process.
Figure 5:
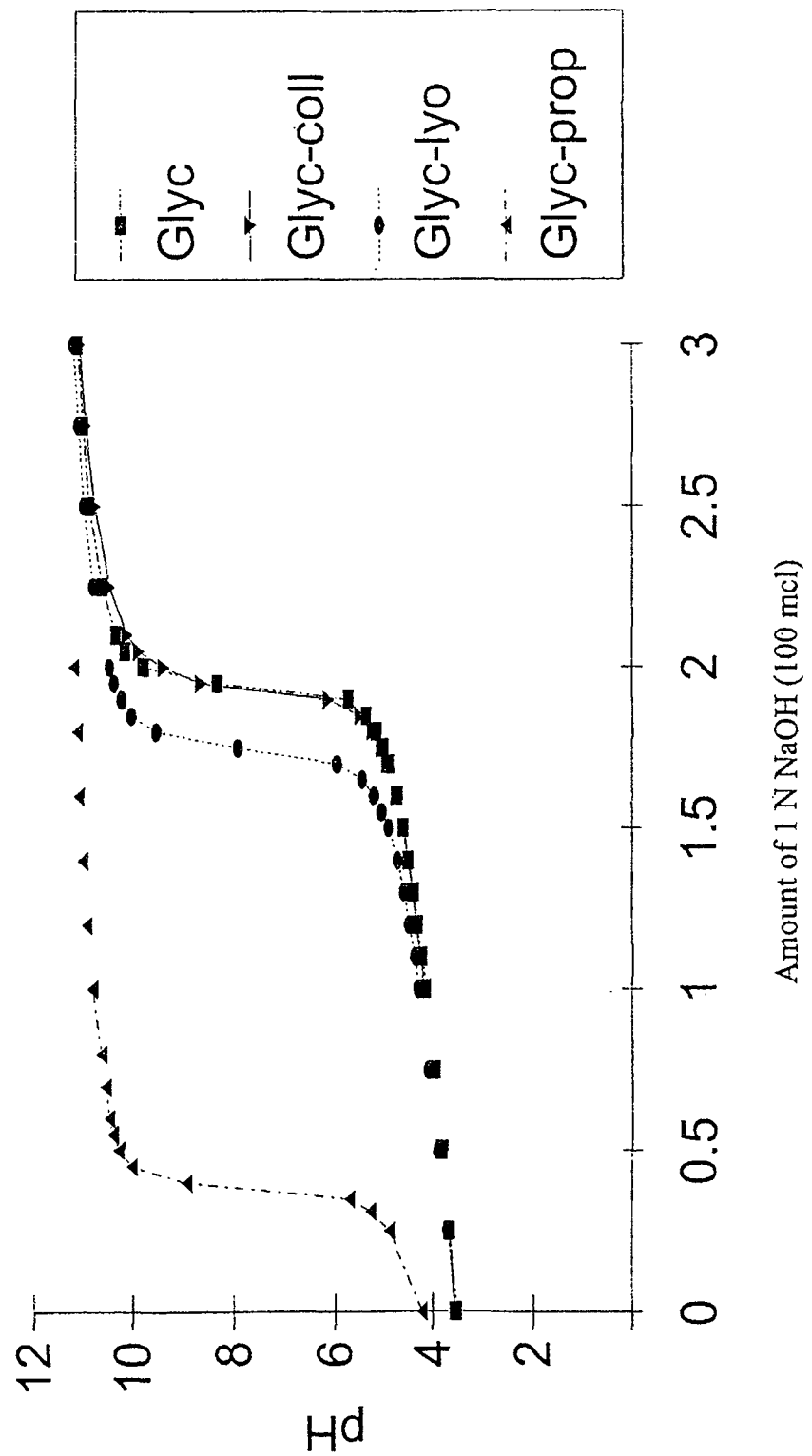
FIG. 5 illustrates volatility of glycolic acid from an implantable material during lyophilization process.

The present invention is directed to a material composition which includes collagen and water. The material of the present invention has a putty consistency and can be molded to a desirable shape. The present invention is also directed to a process for implanting the material in the body for the purpose of stimulating or causing a biological response or activity such as inducing bone formation. Particularly, the material of the present invention is suitable for implanting in humans and animals with an osseous defect to induce the regeneration of osseous tissue to correct the defect.

The collagen component of the present invention is preferably fibrillar collagen, atelopeptide collagen, telopeptide collagen or tropocollagen and can be collected from a variety of mammalian sources. Methods for preparing atelopeptide collagen and tropocollagen are described by Glowacki et al., U.S. Pat. No. 4,440,750, which is incorporated herein in its entirety. Preferably, the collagen is a mammalian collagen. More preferably, the collagen is selected from the group consisting of bovine Type I collagen, and porcine Type I collagen, and most preferably from the group consisting of purified fibrillar bovine tendon Type I collagen. Preferably, the amount of collagen present in the materials and compositions of the present invention is from about 1% by weight (not including any water that is added) to about 10% by weight, more preferably from about 2% by weight to about 8% by weight, and most preferably from about 3% by weight to about 5% by weight.

Materials and compositions of the present invention have a pH of between about 3 and about 6, more preferably between about 3.5 and about 5, and most preferably between about 3.8 and about 4.6. The pH of the material is measured by placing a flat pH electrode on the surface of the material using Ross flat surface electrode available from Orion Co. (Boston, Mass.). It has been found that when the pH is within the limitations identified above, the materials have excellent physical properties, such as a putty consistency which is elastic and dough-like. At higher pH, the materials become crumbly with the consistency of wet sand. A putty consistency is desired because it provides many benefits such as enhanced cohesiveness, ease of handling and moldability. Because materials of the present invention are cohesive, they are also believed to provide the benefit of maintaining an active compound at the site of implantation longer than comparative materials with less cohesiveness.

A desired pH of the material of the present invention can be achieved by forming the material by adding an acid to collagen. As used in this invention, the term "acid" refers to a compound which has lower pKa than water, and the term "acidic proton" refers to a proton whose pKa is lower than water. Suitable acids for use in the present invention include organic acids, such as phenols and carboxylic acids, and inorganic acids, such as hydrochloric acid, phosphoric acid or sulfuric acid. Preferably, the acid is organic acid, hydrochloric acid, or phosphoric acid. Preferably, the acid is selected from the group consisting of acetic acid, ascorbic acid, aspartic acid, benzoic acid, citric acid, glutamic acid, glycolic acid, hydrochloric acid, lactic acid, malic acid, phosphoric acid, salicylic acid, and tartaric acid. More preferably, the acid is selected from the group consisting of ascorbic acid (i.e., vitamin C), acetic acid, acetyl salicylic acid, benzoic acid, citric acid, glutamic acid, glycolic acid, lactic acid, malic acid, salicylic acid, and hydrochloric acid. Most preferably, the acid is selected from the group consisting of ascorbic acid, citric acid, malic acid and lactic acid.

The acid should be added in a sufficient amount to produce a material with acceptable physical properties. Preferably, the amount of acid present in the material is from about 0.05 equivalent mmole (eq. mmol) of acid per 100 mg of collagen to about 2.30 eq. mmol of acid per 100 mg of collagen, more preferably from about 0.1 eq. mmol of acid per 100 mg of collagen to about 1.5 eq. mmol of acid per 100 mg of collagen, and most preferably from about 0.2 eq. mmol of acid per 100 mg of collagen to about 1.5 eq. mmol of acid per 100 mg of collagen. The term "equivalent mmole" refers to the amount of acid, in mmole, divided by the number of acidic protons present per molecule of the acid. For example, some acids such as malic acid have two equivalent acidic protons per molecule; therefore, the preferred amount of malic acid or any other acid having two acidic protons per molecule of acid is one-half that of acids having only one acidic proton. For example, 5 mmol of malic acid and 10 mmol of acetic acid can both be expressed as 10 eq. mmol of acid because malic acid has two acidic protons while acetic acid has only one acidic proton.

Another way to characterize the amount of acid present in the material is in terms of the amount of the acid per 100 mg of collagen. Thus, for example, for a material composition including ascorbic acid, it is preferred that from about 20 mg to about 200 mg of ascorbic acid is added per about 100 mg of collagen, more preferably from about 26 mg to about 131 mg of ascorbic acid per about 100 mg of collagen, and most preferably from about 65 mg to about 131 mg of ascorbic acid per about 100 mg of collagen. It should be appreciated that the amount of the acid will vary depending on its molecular weight. In the event that material is lyophilized, acid can be volatilized during lyophilization which affects the pH and the consistency of the material when the dry solid is reconstituted with water. Materials having, for example, ascorbic acid or malic acid are particularly well suited for lyophilization due to the low volatility of these acids during this process. It is preferred that the amount of acid loss during lyophilization process be less than about 30%, more preferably less than about 15%, and most preferably less than about 5%.

As discussed above, materials and compositions of the present invention have good physical properties, such as cohesiveness and retention of shape after implantation. One measure of such physical properties is that materials and compositions of the present invention have a peak resistance force of at least about 10 grams (g), preferably at least about 20 g, and more preferably at least about 30 g. As used herein, a "peak resistance force" (i.e., peak force) refers to a maximum force exerted by the material when stretched to its breaking point using a TA.XT2 Texture Analyzer apparatus which is available from Texture Technologies Corp. (Scarsdale, N.Y.) or some equivalent apparatus. The material tested is prepared by a SMS/Kieffer molding form and press (TA-105a Texture Technologies) or some equivalent apparatus having a trapezoidal shape measuring 53 mm (I)×4 mm (h)×4 mm (w) at one end and 2.5 mm (w) at the other end.

Another measure of such physical properties is that materials and compositions of the present invention preferably have an extensibility of from about 2 mm to about 25 mm, more preferably from about 3 mm to about 25 mm, and most preferably from about 5 mm to about 25 mm. The term "extensibility" refers to the distance a probe that pulls the material travels until the material breaks when using the same apparatus and the same material dimensions for testing of peak resistance force.

Materials of the present invention can also include an effective amount of an active ingredient. An "active ingredient" refers to any compound or mixture of compounds that have a biological activity. Exemplary active ingredients include osteoinductive materials, growth factors, hormones, antibiotics, and antiviral compounds. Osteoinductive materials are described in detail below. Growth factors can include basic fibroblast growth factor (bFGF) and transforming growth factor beta (TGF-beta) (See Cuevas et al., Basic Fibroblast Growth Factor (FGF) Promotes Cartilage Repair In Vivo, Biochem Biophys Res Commun 156:611-618, 1988). These growth factors have been implicated as cartilage stimulating and angiogenic agents. bFGF, for example, has been shown to increase the rate of osteoblast replication while simultaneously inhibiting their activity (Frenkel S, Singh I J; The effects of fibroblast growth factor on osteogenesis in the chick embryo. In: Fundamentals of bone growth: Methodology and applications. Ed. A D Dixon, B G Samat, D. Hoyte; CRC Press, Boca Raton, Fla., USA, pp. 245-259, 1990). This effect is dose dependent, with higher and lower doses causing decreased activity and middle range doses stimulating activity (Aspenberg P, Thorngren K G, Lohmander L S; Dose-dependent stimulation of bone induction by basic fibroblast growth factor in rats. Acta Orthop Scand 62:481-484, 1991).

The term "effective amount" refers to an amount of an active ingredient sufficient to achieve a desired affect without causing an undesirable side effect. In some cases, it may be necessary to achieve a balance between obtaining a desired effect and limiting the severity of an undesired effect. It will be appreciated that the amount of active ingredient used will vary depending upon the type of active ingredient and the intended use of the composition of the present invention. When the material of the present invention includes an osteogenic material, the amount of osteoinductive material is preferably between about 0.1% by weight and about 10% by weight of the total weight of the putty material, more preferably between about 0.25% by weight and about 4% by weight, and most preferably between about 0.35% by weight and about 1.6% by weight.

An "osteoinductive material" refers to any material that is capable of inducing bone formation (i.e., a material having osteogenic properties) when implanted in a body and includes deminetalized bone matrix and osteoinductive factors. An "osteoinductive factor" refers to a natural, recombinant or synthetic protein or mixture of proteins which are capable of inducing bone formation. For example, the term osteoinductive factor refers to the materials described as bone growth factors in Damien et al., U.S. Pat. No. 5,563,124. It should be noted that while most contemplated applications of the present invention are concerned with use in humans, the products and processes of the present invention work in animals as well. Induction of bone formation can be determined by a histological evaluation showing the de novo formation of bone with accompanying osteoblasts, osteoclasts, and osteoid matrix. For example, osteoinductive activity of an osteoinductive factor can be demonstrated by a test using a substrate onto which material to be tested is deposited. A substrate with deposited material is implanted subcutaneously in a test animal. The implant is subsequently removed and examined microscopically for the presence of bone formation including the presence of osteoblasts, osteoclasts, and osteoid matrix. A suitable procedure is illustrated in Example 5 of U.S. Pat. No. 5,290,763.

No generally accepted scale for evaluating the degree of osteogenic activity exists, however, certain factors are widely recognized as indicating bone formation. Such factors are referenced in the scale of 0-8 which is provided in Table 3 of Example 1 of U.S. Pat. No. 5,563,124. The 0-4 portion of this scale corresponds to the scoring system described in U.S. Pat. No. 5,290,763, which is limited to scores of 0-4. The remaining portion of the scale, scores 5-8, references additional levels of maturation of bone formation. The expanded scale also includes consideration of resorption of collagen, a factor which is not described in U.S. Pat. No. 5,290,763.

Suitable osteoinductive factors of the present invention can be produced by purification of naturally occurring proteins from bone or by recombinant DNA techniques. As used herein, the term recombinantly produced osteoinductive factors refers to the production of osteoinductive factors using recombinant DNA technology. For example, nucleic acids encoding proteins having osteogenic activity can be identified by producing antibodies that bind to the proteins. The antibodies can be used to isolate, by affinity chromatography, purified populations of a particular osteogenic protein. The amino acid sequence can be identified by sequencing the purified protein. It is possible to synthesize DNA oligonucleotides from the known amino acid sequence. The oligonucleotides can be used to screen either a genomic DNA and/or cDNA library made from, for example bovine DNA, to identify nucleic acids encoding the osteogenic protein. The correct oligonucleotide will hybridize to the appropriate cDNA thereby identifying the cDNA encoding the osteogenic protein encoding gene.

Antibodies that bind osteogenic proteins can also be used directly to screen a cDNA expression library. For example, eukaryotic cDNA sequences encoding osteogenic proteins can be ligated into bacterial expression vectors. The expression vectors can be transformed into bacteria, such as E. coli, which express the transformed expression vector and produce the osteogenic protein. The transformed bacteria can be screened for expression of the osteogenic protein by lysing the bacteria and contacting the bacteria with radioactively-labelled antibody.

Recombinant osteoinductive factor can be produced by transfecting genes identified according to the method described above into cells using any process by which nucleic acids are inserted into cells. After transfection, the cell can produce recombinant osteoinductive factors by expression of the transfected nucleic acids and such osteoinductive factors can be recovered from the cells.

A number of naturally occurring proteins from bone or recombinant osteoinductive factors have been described in the literature and are suitable for the present invention. Recombinantly produced osteoinductive factors have been produced by several entities. Creative Biomolecules of Hopkinton, Mass., USA produces a osteoinductive factor referred to as Osteogenic Protein 1 or OP 1. Genetics Institute of Cambridge, Mass., USA produces a series of osteoinductive factors referred to as Bone Morphogenetic Proteins 1-13 (i.e., BMP 1-13), some of which are described in U.S. Pat. Nos. 5,106,748 and 5,658,882 and in PCT Publication No. WO 96/39,170. Purified osteoinductive factors have been developed by several entities. Collagen Corporation of Palo Alto, Calif., USA developed a purified protein mixture which is believed to have osteogenic activity and which is described in U.S. Pat. Nos. 4,774,228; 4,774,322; 4,810,691; and 4,843,063. Marshall Urist of the University of California developed a purified protein mixture which is believed to be osteogenic and which is described in U.S. Pat. Nos. 4,455,256; 4,619,989; 4,761,471; 4,789,732; and 4,795,804. International Genetic Engineering, Inc. of Santa Monica, Calif., USA developed a purified protein mixture which is believed to be osteogenic and which is described in U.S. Pat. No. 4,804,744. All of the foregoing patents are incorporated herein by reference.

A preferred osteoinductive factor of the present invention and process for making the same is described in detail in related U.S. Pat. No. 5,290,763. This osteoinductive factor is particularly preferred because of its high osteogenic activity and because it is a purified osteoinductive factor. The osteoinductive factor of U.S. Pat. No. 5,290,763 exhibits osteoinductive activity at about 3 micrograms when deposited onto a suitable carrier and implanted subcutaneously into a rat. In one embodiment, the osteoinductive factor is an osteoinductively active mixture of proteins which exhibit the gel separation profile shown in FIG. 1 of U.S. Pat. No. 5,563,124. This gel separation profile was obtained using SDS-PAGE. The first column is a molecular weight scale which was obtained by performing SDS-PAGE on standards of known molecular weight. The second column illustrates the SDS-PAGE profile for a mixture of proteins in accordance with the present invention which have been reduced with 2-mercaptoethanol. The third column illustrates the SDS-PAGE profile for a nonreduced mixture of proteins in accordance with the present invention. Although the mixture of proteins which provide the SDS-PAGE profile illustrated therein have been found to have high osteoinductive activity, it is anticipated that mixtures of proteins having SDS-PAGE profiles which differ slightly from that illustrated therein will also be effective. For example, effective protein mixtures can include proteins that differ in molecular weight by plus or minus 5 KD from those shown therein, and can include fewer or greater numbers of proteins than those shown. Therefore, mixtures of proteins having profiles which comprise substantially all of the protein bands detected in the reduced or nonreduced SDS-PAGE profiles therein will be considered to be within the scope of the invention.

Yet another embodiment of the preferred osteoinductive factor of the invention includes an osteoinductively active mixture of proteins having, upon hydrolysis, an amino acid composition of from about 20.7 to about 26.1 mole percent acidic amino acids, about 11.3 to about 15.7 mole percent hydroxy amino acids, about 37.6 to about 42.4 mole percent aliphatic amino acids, about 5.8 to about 7.9 mole percent aromatic amino acids and about 13.3 to about 19.9 mole percent basic amino acids. More particularly, the preferred osteoinductive factor has an amino acid composition of about 20.7 to about 26.1 (preferably about 23.4) mole percent of ASP (+ASN) and GLU(+GLN); about 11.3 to about 15.7 (preferably about 13.5) mole percent SER and THR; about 37.6 to about 42.4 (preferably about 40.0) mole percent ALA, GLY, PRO, VAL, MET, ILE, and LEU; about 5.8 to about 7.9 (preferably about 6.8) mole percent TYR and PHE; and about 13.3 to about 19.9 (preferably about 16.6) mole percent HIS, ARG, and LYS. A further embodiment of the preferred osteoinductive factor is a protein mixture having the approximate amino acid composition shown in Table 1.

TABLE 1

| Amino Acid | Mole Percent |
| --- | --- |
| Asp | 11.14 |
| Glu | 12.25 |
| Ser | 9.48 |
| Gly | 8.50 |
| His | 2.28 |
| Arg | 7.19 |
| Thr | 4.03 |
| Ala | 8.05 |
| Pro | 7.16 |
| Tyr | 3.63 |
| Val | 3.79 |
| Met | 1.73 |
| Ile | 2.75 |
| Leu | 8.00 |
| Phe | 3.21 |
| Lys | 7.11 |

A still further embodiment of the preferred osteoinductive factor is a protein mixture obtained by any of the purification processes described in U.S. Pat. No. 5,290,763.

Materials of the present invention are typically derived by admixing collagen, water and an acid. As discussed above, the material can also include other substances such as an active ingredient. The material can also be sterilized by dialysis, irradiation (e.g. using g-radiation), filtration, chemical treatment (e.g., using ethylene oxide), or other known sterilization methods. Alternatively, the material which can be a gel is lyophilized to a dry solid before being sterilized. When sterilizing the material using a chemical treatment, it is preferred that the material be lyophilized to a dry solid prior to being sterilized. Lyophilization removes water and prevents any chemical reaction which may occur between the chemical used for sterilization (e.g., ethylene oxide) and water. Another alternative method is to make the material of the present invention in an aseptic environment, thereby eliminating the need for a separate sterilization step.

Materials of the present invention can also include demineralized bone material. A method for preparing demineralized bone material in a particulate form is described by Glowacki et al., U.S. Pat. No. 4,440,750. Alternatively demineralized bone material can be prepared by grinding a bone, demineralizing it with 0.6 M HCl solution, washing with a phosphate buffered solution, washing with ethanol and drying it. Demineralized bone material can also be obtained from a commercial bone or tissue bank, for example, from AlloSource (Denver, Colo.).

Materials of the present invention can be part of a kit containing the components of the materials. Such kits are particularly useful for health care professionals in preparing the materials and compositions of the present invention immediately before use. Such kits, in addition to including the component parts of the various materials and compositions of the invention also include one or more containers for mixing the components, along with optional mixing devices such as stirrers. Further, such kits can include the components in sealed, pre-measured packages. The sealed packages can be sealed aseptically and the amounts of the components can be pre-measured in relative amounts as described elsewhere herein.

Another aspect of the present invention includes a process of implanting a material or composition as broadly described above into a body. As noted above, most uses of the present invention are concerned with human application. The process, however, is applicable to a wide variety of animals, particularly mammals. As used in this invention, the term "implanting" refers to placing the material or composition of the present invention in an area in which it is desired to achieve the activity of the active ingredient. In this embodiment of the present invention, the materials function as a delivery vehicle for an active ingredient. Such methods of implantation can involve a surgery or a simple injection of the product using any of the known methods including a use of syringe.

For the product of the present invention comprising an osteogenic composition, the present material and process can be used in a variety of application whenever there is a need to generate bone. Such applications include induction of bone formation for hip replacement operations, knee replacement operations, spinal fusion procedures, repair of periodontal defects, treatment of osteoporosis, repair of bone tumor defects, dental procedures, repair of cranial maxilla facial defects, and repair of bone fractures.

In the case of hip replacement operations, the ball and socket joint of a hip is replaced when a person's hip is not functioning properly. The ball portion of a joint is replaced by surgical removal of the ball portion from the terminus of the femur. The artificial ball portion has a functional ball end with the opposite end being a spike which is inserted into the proximal end of the femur from which the natural ball portion was removed. The spike can have a porous surface so that bone growth around the spike can anchor the spike in the femur. Materials of the present invention can be layered or packed between the spike and the cavity in the femur in which spike is to be inserted. The socket portion of a joint is replaced by inserting an artificial socket into the natural socket. The artificial socket is sized to fit with the artificial ball. On the surface of the artificial socket which contacts the natural socket, the artificial socket can have a porous surface. Materials of the present invention can be placed in the natural socket cavity so that upon placement of the artificial socket, the material is between the natural and artificial socket. In this manner, as bone is formed, the artificial socket is anchored in the natural socket.

Materials of the present invention are also suitable for use in knee replacement operations. Knee prostheses have a femoral and a tibial component which are inserted into the distal end of the femur and the surgically prepared end of the tibia, respectively. Materials of the present invention can be layered or packed between the femoral and/or tibial components of the prosthesis and the respective portions of the femur and tibia. In this manner, as bone formation is induced between the prosthesis and the bones, the prosthesis becomes anchored.

Materials of the present invention are also suitable for use in spinal fusion operations in which it is desired to substantially immobilize two vertebrae with respect to each other. The material can be applied, for example, between adjacent spinous and transverse processes so that upon bone formation throughout the material, two adjacent vertebrae are joined by fusion between the respective spinous processes and transverse processes.

Materials of the present invention can also be used in spinal fusion operations in which it is desired to substantially immobilize two vertebrae with respect to each other by using metal cages or equivalent implants. In this case, the cages are placed in the disk space between two vertebral bodies, and the material of the present invention is packed into and around the cages to obtain bone formation through and around the cages thus fusing two vertebrae and stabilizing the spine.

EXAMPLES

Unless otherwise stated, following general procedures were used throughout the Examples.

Bovine demineralized bone material was prepared by grinding bovine bone to a particle size of about 125 μm to about 850 μm. It was demineralized in 0.6 M HCl, washed with phosphate buffered solution, rinsed with ethanol and dried.

The putty materials were tested using TA-XT2 Texture Analyzer having following testing parameters: pre-test speed=2.0 mm/sec, test speed=3.3 mm/sec, post test speed=10.0 mm/s, distance=30 mm, trigger force=3 g.

The pH of putty materials were measured using Ross flat surface electrode available from Orion Co. (Boston, Mass.).

Example 1

This example illustrates the effect of acid on the consistency of the material produced when combined with collagen and demineralized bone material.

For each acid and molarity concentration tested, a gel was prepared by mixing 100 mg of purified bovine tendon Type I collagen and 7.4 mL of aqueous acid solution. The gel was lyophilized and then mixed with water and about 2.1 g to about 2.4 g of demineralized bone material. The resulting composition was qualitatively evaluated for its physical properties by manual examination for properties such as cohesiveness, elasticity and moldability. Each gel was graded as having acceptable physical properties or not. Some acids, such as ascorbic acid and benzoic acid, showed a wide range of useful concentrations in producing a composition having acceptable physical properties, while others such as acetic acid and lactic acid showed a narrow range of amount which is suitable for producing a composition with putty consistency. If a gel was found to initially have acceptable physical properties, it was then subjected to ethylene oxide sterilization and re-evaluated. Table 2 summarizes the qualitative evaluation of the compositions tested.

TABLE 2

| Acid | mM (mequiv.) | Avg. pH (w/DBM) | Acceptable Physical Properties | Post ethylene oxide Acceptable Physical Properties |
|---|---|---|---|---|
| Acetic Acid | 6.67 (0.007) | 5.95 | N | N/A |
| " | 33.3 (0.037) | 4.97 | N | N/A |
| " | 50.0 (0.056) | N/R | N | N/A |
| " | 66.6 (0.074) | 4.85 | N | N/A |
| " | 100 (0.111) | N/R | Y | N |
| " | 167 (0.185) | 4.51 | Y | N |
| " | 333 (0.370) | 4.09 | Y | N/A |
| Ascorbic Acid | 10 (0.074) | N/R | N | N |
| " | 20 (0.148) | N/R | Y/N | N |
| " | 30 (0.222) | 4.33 | Y | Y |
| " | 50 (0.370) | 4.10 | Y | Y |
| " | 100 (0.740) | N/R | Y | Y |
| " | 50 (0.370) | 4.46 | Y | N/A |
| " | 50 (0.370) | 4.64 | N | N/A |
| " | 50 (0.370) | N/R | N | N/A |
| " | 50 (0.370) | N/R | N | N/A |
| Aspartic Acid | 30 (0.444) | N/R | N | N/A |
| Benzoic Acid | 10 (0.074) | N/R | N | N |
| " | 25 (0.185) | N/R | Y | N |
| Citric Acid | 10 (0.148) | N/R | N | |
| " | 20 (0.298) | N/R | N | N/A |
| " | 50 (0.740) | N/R | Y | N |
| " | 100 (1.480) | 3.58 | Y | N |
| " | 100 (1.480) | 3.77 | Y | N/A |
| " | 100 (1.480) | 3.95 | Y/N | N/A |
| " | 100 (1.480) | 4.05 | N | N/A |
| Glutamic Acid | 10 (0.148) | N/R | N | N/A |
| " | 100 (1.480) | N/R | N | N/A |
| Glycolic Acid | 100 (0.659) | N/R | Y | N |
| Hydrochloric Acid | 10 (0.074) | 5.76 | Y/N | N |
| " | 100 (0.740) | N/R | N | N/A |
| Lactic Acid | 1.9 (0.010) | 6.50 | N | N/A |
| " | 9.4 (0.051) | 6.17 | N | N/A |
| " | 10 (0.054) | N/R | N | N/A |
| " | 24 (0.130) | 5.18 | Y/N | N/A |
| " | 30 (0.162) | 4.09 | Y | N/A |
| " | 47 (0.254) | 4.48 | Y | N/A |
| " | 60 (0.324) | 3.94 | Y | N |
| " | 100 (0.540) | N/R | N | N/A |
| " | 100 (0.540) | 4.38 | N | N/A |
| " | 100 (0.540) | 4.55 | N | N/A |
| " | 100 (0.540) | 4.85 | N | N/A |
| " | 100 (0.540) | 5.17 | N | N/A |
| " | 100 (0.540) | 5.56 | N | N/A |
| " | 188 (1.016) | 3.75 | Y/N | N/A |
| Malic Acid | 10 (0.148) | N/R | N | N/A |
| " | 30 (0.444) | 4.00 | Y | N/A |
| " | 50 (0.740) | 3.77 | Y | N |
| " | 100 (1.48) | N/R | Y | N/A |
| Phosphoric Acid | 5.4 (0.80) | 6.11 | N | N/A |
| " | 10.8 (0.160) | 5.91 | N | N/A |
| " | 50 (0.740) | N/R | Y | N/A |
| " | 100 (1.480) | N/R | N | N/A |
| Salicylic Acid | 10 (0.074) | N/R | Y | N |
| Tartaric Acid | 100 (1.480) | N/R | Y | N/A |

N/R = not recorded,
N/A = not applicable (not tested) and
Y/N = marginally acceptable results.

Example 2

This example illustrates the amount of acid loss during lyophilization of compositions and the physical properties of the resulting material before and after ethylene oxide sterilization.

A control solution of 500 μL of a 1 M solution of the acids tested in 100 mL of water was titrated with 1 N NaOH solution. To test for the amount of acid loss during lyophilization, samples were prepared using the procedure of Example 1, except that no demineralized bone material was added after lyophilization. The resulting material was dissolved in water (at a ratio of 1 g of lyophilized material/100 mL), and titrated with 1 N NaOH solution. The materials, except the one made with acetic acid were subsequently treated with 2-propanol and titrated as follows. The lyophilized samples of collagen/acid mixture were chopped in 2-propanol and relyophilized to free much of the acid which was then removed by the second lyophilization as evidenced when the samples were titrated after this treatment. The results of titrations curves for materials made with ascorbic acid, malic acid, acetic acid, lactic acid and glycolic acid are shown in FIGS. 1-5, respectively. The amount of acid loss and the amount of acid remaining in the samples are shown on Table 3.

TABLE 3

| Acid | mM | % Acid loss | mg Acid in sample | wt % of acid in sample |
|---|---|---|---|---|
| Acetic Acid | 50 | 85 | 3.33 | 3.2 |
| Ascorbic Acid | 10 | 0 | 13.03 | 11.5 |
| " | 20 | 0 | 26.07 | 20.7 |
| " | 50 | 0 | 65.17 | 39.5 |
| " | 100 | 0 | 130.34 | 56.6 |
| Citric Acid | 10 | 0 | 14.22 | 12.4 |
| " | 20 | 0 | 28.43 | 22.1 |
| " | 50 | 0 | 71.08 | 41.5 |
| " | 100 | 0 | 142.17 | 58.7 |
| Hydrochloric Acid | 10 | ? | 2.70 | 2.6 |
| Lactic Acid | 50 | 27 | 24.33 | 19.6 |
| " | 100 | 27 | 48.66 | 32.7 |
| Glycolic Acid | 50 | 11 | 28.14 | 22.0 |
| " | 100 | 11 | 56.28 | 36.0 |
| Malic Acid | 50 | 0 | 49.61 | 33.2 |
| " | 100 | 0 | 99.23 | 49.8 |

These results indicate that ascorbic acid, citric acid and malic acid were of relatively low volatility and acetic acid was found to be the most volatile.

Example 3

This example illustrates bioactivity of the implantable materials having various acids.

A gel was prepared by mixing 100 mg of collagen, 7.4 mL of aqueous acid solution of a given molarity, and a given amount of bone growth protein (BGP) as described in U.S. Pat. No. 5,290,763. The gel was lyophilized and some of the lyophilized gels were sterilized by contacting with ethylene oxide. About 15 mg of lyophilized gel is mixed with 1.14 mL of water and 173 mg of rat demineralized bone material. The resulting material was placed in a mold and 12 to 15 disks of 7 mm diameter and 2 mm thickness was formed. The disks were frozen, lyophilized overnight, and implanted subcutaneously in rats. The animals were sacrificed after 28 days and histological slides were made of the explanted tissues. Acid fuchsin and Sanderson's Rapid Bone Stain or toluidine blue were used to stain the explanted tissue slides to facilitate viewing of bone and cartilage formation. The type and molarity of each acid tested, the amount of BGP added, and whether the gel was exposed to ethylene oxide are set forth in Table 4.

TABLE 4

| Acid | mM | BGP (μg) | Ethylene oxide exposure? |
|---|---|---|---|
| H₂O (control) | — | 20 | Y |
| Ascorbic Acid | 10 | 20 | Y |
| " | 20 | 20 | Y |
| " | 30 | 20 | Y |
| " | 50 | 0 | N |
| " | 50 | 10 | N |
| " | 50 | 20 | Y |
| " | 50 | 3.5 | N |
| " | 50 | 35 | N |
| " | 50 | 8 | N |
| " | 100 | 20 | Y |
| Benzoic Acid | 25 | 20 | Y |
| Citric Acid | 50 | 20 | Y |
| Glycolic Acid | 50 | 10 | N |
| " | 50 | 20 | Y |
| Lactic Acid | 50 | 20 | Y |
| " | 100 | 10 | N |
| Malic Acid | 50 | 10 | N |
| " | 50 | 20 | Y |

Materials made with lactic acid at 50 mM and 100 mM, and ascorbic acid at 10 mM, 20 mM, 30 mM, 50 mM and 100 mM showed good complete ossicle formation. Bone was seen throughout the explanted tissue. There was generally a mature rim of bone and an occasional pocket of soft tissue. Results of materials made with malic acid at 50 mM, glycolic acid at 50 mM, citric acid at 50 mM and benzoic acid at 25 mM varied from sparse islands to full ossicles. The sensitivity of the osseoinductive response to BGP does was evaluated with ascorbic acid at 50 mM. The results showed no bone formation at 0 BGP, and at 35 μg, significantly larger amounts of bone growth occurred. The results also indicate that, after ethylene oxide exposure, the osseoinductive response appears to be inversely related to the molarity of the acid. Good bone formation was observed where ascorbic acid at 30 mM and 50 mM was added to a mixture of collagen and BGP that had not been exposed to ethylene oxide, even where the ascorbic acid had itself been exposed separately to ethylene oxide. Good bone formation was observed in samples made using 10 mM and 20 mM ascorbic acid, regardless of whether it was exposed to ethylene oxide or not.

Example 4

This example illustrates the effect of adding an acidic buffer solution to a lyophilized collagen material just prior to addition of the demineralized bone matrix.

Instead of preparing the collagen with the acid solution and then lyophilizing the material as described in Experiment 1, a sample of collagen was prepared with a dilute, volatile acid (e.g., acetic acid) and iyophilized. This material when reconstituted with water resulted in subjectively poor handling properties and could not be tested objectively using the methods described in the following examples. When the same material was reconstituted by adding an acid buffer solution instead of water, the resulting material was in a putty form that was both subjectively adequate and was testable using the experimental procedures described in the following examples. A variety of acid buffer solutions, including ascorbic acid at 20, 30, 50 and 100 mM, citric acid at 50 mM, malic acid at 50 mM, and lactic acid at 50 mM, can be used as an acid buffer solution in reconstituting the lyophilized collagen to obtain a material having a desired physical properties.

Example 5

This example illustrates effect of different acids in extensibility and peak resistance force (peak force) of a material.

Gels were prepared and lyophilized using the procedure of Example 4. Lyophilized gels were refrigerated until use.

Samples for physical property testing were prepared by adding 6 mL of water to the lyophilized gel. About 1.75 g of bovine demineralized bone material having a particle size of from 125 μm to about 850 μm was added, mixed and allowed to stand for about 5 minutes, unless otherwise noted. The putty was then placed in an SMS/Kieffer molding form and press (TA-105a Texture Technologies). This produced test specimens having a trapezoidal shape measuring 53 mm (l)×4 mm (h)×4 mm (w) at one end and 2.5 mm (w) at the other end. Table 5 shows a peak force and a distance to peak force measured using TA-XT2 texture analyzer with test rate (i.e., rate of probe travel) of 2.0 mm/sec and trigger force of 5.0 g for putty materials having a various acid solutions.

TABLE 5

| Acid | Distance (mm) | Peak Force (g) |
| --- | --- | --- |
| 50 mM Ascorbic Acid | −6.75 ± 0.48 | 58.21 ± 5.11 |
| 50 mM Acetic Acid | −0.93 ± 0.07 | 6.65 ± 0.23 |
| 50 mM Citric Acid | −10.83 ± 0.67 | 39.72 ± 5.41 |
| 10 mM HCl | −4.25 ± 0.16 | 20.24 ± 2.54 |
| 50 mM Lactic Acid | −7.50 ± 0.35 | 49.28 ± 4.45 |

Without being bound by a theory, the poor result of 50 mM acetic acid sample is believed to be due to the volatility of acetic acid during lyophilization process where about 85% of the acetic acid is lost.

Example 6

This example illustrates the effect of different acid concentration on the physical property of a putty material.

Samples using solution of a various concentrations of ascorbic acid and citric acid were prepared and tested using the procedure of Example 6. The results are shown in Table 5. In general, as the concentration of acid increases the extensibility of the putty material increases.

TABLE 6

| Acid | pH | Distance (mm) | Peak Force (g) |
| --- | --- | --- | --- |
| 10 mM Ascorbic Acid | 5.7 | −1.74 ± 0.49 | 38.84 ± 20.69 |
| 20 mM Ascorbic Acid | 5.0 | −3.58 ± 0.18 | 80.31 ± 24.65 |
| 50 mM Ascorbic Acid | 4.6 | −6.21 ± 0.34 | 47.55 ± 12.09 |
| 100 mM Ascorbic Acid | 4.1 | −6.96 ± 0.81 | 40.28 ± 8.82 |
| 10 mM Citric Acid | 5.0 | −3.25 ± 1.37 | 26.39 ± 11.15 |
| 20 mM Citric Acid | 4.6 | −4.78 ± 0.46 | 71.49 ± 15.98 |
| 50 mM Citric Acid | 4.1 | −11.74 ± 0.89 | 88.71 ± 11.19 |
| 100 mM Citric Acid | 3.3 | −11.55 ± 0.76 | 42.41 ± 3.36 |

Example 7

This example illustrates the effect of preparation time on the pH, distance to peak force and peak force of a putty material.

Samples using 50 mM ascorbic acid, 50 mM citric acid and 100 mM citric acid solutions were prepared and tested using the procedure of Example 5. Stand times for the putty materials were varied at 2, 5, 10 and 20 minutes. The results are shown on Table 7.

TABLE 7

| Acid | time (min) | Distance (mm) | Peak Force (g) |
| --- | --- | --- | --- |
| 50 mM Ascorbic Acid | 2 | −11.75 ± 0.43 | 54.51 ± 4.82 |
| " | 5 | −12.87 ± 2.30 | 56.90 ± 6.25 |
| " | 10 | −10.53 ± 0.52 | 74.21 ± 7.24 |
| " | 20 | −8.40 ± 0.80 | 58.11 ± 7.82 |
| 50 mM Citric Acid | 2 | −17.56 ± 1.82 | 35.30 ± 2.34 |
| " | 5 | −18.56 ± 3.17 | 49.49 ± 5.12 |
| " | 10 | −16.66 ± 1.50 | 54.74 ± 6.42 |
| " | 20 | −18.32 ± 1.24 | 55.13 ± 8.53 |
| 100 mM Citric Acid | 2 | −11.32 ± 0.62 | 21.61 ± 4.13 |
| " | 5 | −10.54 ± 0.32 | 19.32 ± 1.58 |
| " | 10 | −10.79 ± 0.66 | 25.87 ± 3.90 |
| " | 20 | −14.42 ± 1.10 | 31.84 ± 4.26 |

Distance to peak force are similar for putty materials having a stand time of 2, 5 and 10 minutes. More importantly, the pH of the putty materials changed slightly with time as shown on Table 8.

TABLE 8 pH of Putty Materials over Time

| Acid (amount of acid) | 2 min | 5 min | 10 min | 20 min |
| --- | --- | --- | --- | --- |
| 50 mM Ascorbic Acid (65.2 mg) | 4.4 | 4.3 | 4.5 | 4.6 |
| 50 mM Citric Acid (71.1 mg) | 3.8 | 3.9 | 4.0 | 4.0 |
| 100 mM Citric Acid (142.2 mg) | 3.4 | 3.3 | 3.4 | 3.5 |

Example 8

This example illustrates the effect of ethylene oxide sterilization on the physical properties of putty materials.

Samples using 20 mM and 50 mM ascorbic acid, and 50 mM and 100 mM citric acid solutions were prepared using the procedure of Example 5 and sterilized with ethylene oxide by MMC (Erie, Pa.). A comparative distance to peak force and peak force are shown on Table 9.

TABLE 9

Effect of Ethylene Oxide Sterilization

| Acid | Sterilized? | pH | Distance (mm) | Peak Force (g) |
| --- | --- | --- | --- | --- |
| 20 mM Ascorbic Acid | Y | 5.0 | −4.30 ± 0.34 | 8.22 ± 1.53 |
| " | N | 4.9 | −5.11 ± 1.26 | 13.57 ± 4.13 |
| 50 mM Ascorbic Acid | Y | 4.4 | −9.30 ± 1.13 | 18.49 ± 1.68 |
| " | N | 4.3 | −12.54 ± 1.32 | 56.17 ± 7.91 |
| 50 mM Citric Acid | Y | 4.1 | 0 | <3 |
| " | N | 3.8 | −16.24 ± 1.47 | 50.98 ± 4.12 |
| 100 mM Citric Acid | Y | — | 0 | <3 |
| " | N | 3.4 | −11.99 ± 0.67 | 25.17 ± 1.01 |

Example 9

This example illustrates the changes in physical properties of putty materials due to sterilization by exposure to g-radiation.

Samples using 20 mM, 50 mM and 100 mM ascorbic acid solutions were prepared using the procedure of Example 5 and irradiated with 1.0 MRad of g-radiation by Sterigenics (Charlotte, N.C.). A comparative distance to peak force and peak force are shown on Table 10.

TABLE 10

| | | Effect of g-radiation | | |
|---|---|---|---|---|
| Acid | Sterilized? | pH | Distance (mm) | Peak Force (g) |
| 20 mM Ascorbic Acid | Y | 5.2 | 0 | <3 |
| 20 mM Ascorbic Acid | N | 5.0 | −2.94 ± 1.22 | 5.83 ± 1.2 |
| 50 mM Ascorbic Acid | Y | 4.6 | −6.53 ± 0.71 | 27.52 ± 3.03 |
| 50 mM Ascorbic Acid | N | 4.4 | −7.48 ± 1.05 | 38.81 ± 5.80 |
| 100 mM Ascorbic Acid | Y | 4.1 | −9.02 ± 0.16 | 18.80 ± 1.70 |
| 100 mM Ascorbic Acid | N | 4.1 | ... −11.79 ± 0.26 | 38.92 ± 1.13 |

Samples prepared with 50 mM or 100 mM ascorbic acid retained its putty texture even after being exposed to g-radiation.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An implantable moldable putty material for delivery of an active ingredient to a patient comprising collagen and a first acidic solution having a pH between about 3 and about 6, wherein the collagen has been combined with a sufficient amount of the first acidic solution and formed the moldable putty material, wherein the collagen was previously processed by combining the collagen with a second acidic solution and lyophilizing the combined collagen and second acidic solution; wherein the first acidic solution includes an acid different from an acid included in the second acidic solution, wherein said putty material has at least one physical property selected from the group consisting of a peak resistance force of at least about 10 g and an extensibility of from about 2 mm to about 25 mm.

2. The implantable putty material of claim 1, wherein said collagen is selected from the group consisting of fibrillar collagen, atelopeptide collagen, telopeptide collagen and tropocollagen.

3. The implantable putty material of claim 1, wherein said collagen is bovine tendon Type I collagen.

4. The implantable putty material of claim 1, wherein said first acidic solution comprises from about 20 mM to about 100 mM of an acid selected from the group consisting of ascorbic acid, citric acid, lactic acid, and malic acid.

5. The implantable putty material of claim 4, wherein said acid is ascorbic acid.

6. The implantable putty material of claim 1, wherein said putty material further comprises an active ingredient.

7. The implantable putty material of claim 6, wherein said active ingredient is selected from the group consisting of osteoinductive materials, growth factors, cartilage inducing factors, angiogenic factors, hormones, antibiotics, and antiviral compounds.

8. The implantable putty material of claim 1, wherein the collagen is present in an amount from about 1% dry weight to about 10% dry weight.

9. The implantable putty material of claim 1, wherein the pH is between about 3.5 and about 5.

10. The implantable putty material of claim 7, wherein the growth factor is selected from the group consisting of basic fibroblast growth factor (bFGF) and transforming growth factor beta (TGF-β).

11. The implantable putty material of claim 7, wherein the osteoinductive factor is selected from the group consisting of bone growth protein (BGP), bone morphogenetic protein-1 (BMP-1), BMP-2, BMP-3, and osteogenic protein 1 (OP-1).

12. The implantable putty material of claim 11, wherein the osteoinductive factor is natural, recombinant, or synthetic.

13. The implantable putty material of claim 12, wherein the osteoinductive factor is natural and derived from bovine long bones.

14. The implantable putty material of claim 1, further comprising demineralized bone material (DBM).

15. The implantable material of claim 14, wherein the collagen is present in an amount from about 1% dry weight to about 10% dry weight and the DBM is present in an amount from about 92% dry weight to about 96% dry weight.

16. The implantable putty material of claim 1, wherein the second acidic solution is acetic acid.

17. The implantable putty material of claim 6 wherein the active ingredient is an osteoinductive material.

18. The implantable putty material of claim 16, wherein said acetic acid is 50 mM acetic acid.

* * * * *